United States Patent [19]

Shaked et al.

[11] Patent Number: 5,037,644
[45] Date of Patent: Aug. 6, 1991

[54] PHARMACEUTICAL COMPOSITIONS OF RECOMBINANT INTERLEUKIN-2 AND FORMULATION PROCESSES

[75] Inventors: Ze'ev Shaked, Berkeley; Tracy Stewart, San Francisco; James W. Thomson, Albany; Pamela Hirtzer, Oakland, all of Calif.

[73] Assignee: Cetus Corporation, Emveryville, Calif.

[21] Appl. No.: 101,175

[22] Filed: Sep. 30, 1987

Related U.S. Application Data

[63] Continuation-in-part of Ser. No. 923,383, Oct. 27, 1986.

[51] Int. Cl.$^5$ .................................. A61K 37/02
[52] U.S. Cl. ........................... 424/85.2; 424/85.1; 530/351; 514/2; 514/970; 514/8; 514/12; 514/21
[58] Field of Search ............... 530/351; 514/2, 8, 12, 514/21, 970; 424/85.1, 85.2

[56] References Cited

U.S. PATENT DOCUMENTS

| | | | |
|---|---|---|---|
| 3,919,411 | 11/1975 | Glass et al. | 424/88 |
| 4,179,337 | 12/1979 | Davis et al. | 435/181 |
| 4,343,735 | 8/1982 | Menge et al. | 530/351 |
| 4,457,916 | 7/1984 | Hayashi et al. | 424/85.2 |
| 4,460,574 | 7/1984 | Yobrov | 424/85.6 |
| 4,507,281 | 3/1985 | Asculai et al. | 424/85.7 |
| 4,604,377 | 8/1986 | Fernandes et al. | 424/85.2 |
| 4,606,917 | 8/1986 | Eppstein | 435/68 |
| 4,645,830 | 2/1987 | Yasushi et al. | 530/351 |
| 4,647,454 | 3/1987 | Cymbalista | 530/351 |
| 4,675,184 | 6/1987 | Hasegawa et al. | 424/85.4 |
| 4,680,175 | 7/1987 | Estis et al. | 424/85.4 |
| 4,772,466 | 9/1988 | Allison et al. | 424/92 |
| 4,797,474 | 1/1987 | Patroni et al. | 530/351 |
| 4,822,605 | 4/1989 | Powell | 424/85.2 |

FOREIGN PATENT DOCUMENTS

| | | |
|---|---|---|
| 092918 | 11/1983 | European Pat. Off. |
| 107498 | 5/1984 | European Pat. Off. |
| 133767 | 3/1985 | European Pat. Off. |
| 135171 | 3/1985 | European Pat. Off. |
| 152345 | 8/1985 | European Pat. Off. |
| 154316 | 9/1985 | European Pat. Off. |
| 196203 | 10/1986 | European Pat. Off. |
| 215658 | 3/1987 | European Pat. Off. |
| 0229016 | 7/1987 | European Pat. Off. |
| 231132 | 8/1987 | European Pat. Off. |
| 0233629 | 8/1987 | European Pat. Off. |
| 233629 | 8/1987 | European Pat. Off. |
| 257890 | 3/1988 | European Pat. Off. |
| 0257956 | 3/1988 | European Pat. Off. |
| 61-67637 | 3/1986 | Japan |
| 61-293926 | 12/1986 | Japan |

OTHER PUBLICATIONS

Chem. Abs., 106:373 (1987) No. 107907K.
Chem. Abs., 94:312 (1981) No. 20423J.
Derwent Publication 84-231892/38 (Abstract only).
Proc. Natl. Acad. Sci. U.S.A., 77, No. 10:6134-6138 (1980).
Wang et al., J. Parenteral Drug Assoc., 34:452-462 (1980).
Morikawa et al., Cancer Research, 47:37-41 (Jan. 1, 1987).
Mier et al., J. Immunol., 128(3):1122-1127 (Mar. 1982).
Harel-Bellan et al., J. Immunol. Methods, 64:61-69 (1983).
J. Sedmak, Methods in Enzymology, 78:591-595 (1981).
J. Heine et al., Archives of Virology, 57:185-188.
Edelman, Rev. Infect. Dis., vol. 2(3), 1980, pp. 370-383.
Gearing et al., Lymphokine Res 5, 1986, pp. 519-521.

Primary Examiner—Garnette D. Draper
Attorney, Agent, or Firm—Philip L. McGarrigle; Leona L. Lauder; Albert P. Halluin

[57] ABSTRACT

Stable pharmaceutical compositions suitable for parenteral administration to animals or humans are prepared comprising a therapeutically effective amount of a recombinant interleukin-2 (IL-2) protein dissolved in an inert carrier medium comprising one or more biocompatible non-ionic polymeric detergents which act as solubilizer/stabilizers for the claimed formulations.

23 Claims, 8 Drawing Sheets

IL-2 PROCESS

| Step | Conditions |
|---|---|
| Fermentation | |
| Cel concentration | |
| Cell wall and membrane disruption | distilled water |
| Diafiltration | 5 mM EDTA |
| Redisruption | 2 mM EDTA 1% octanol (v/v) |
| Sucrose suspension | 15-35% sucrose (w/w) |
| Centrifugation | 10,000-20,000 x g |
| Paste solubilization | 5% SDS, phosphate buffered saline |
| Centrifugation | 25,000-35,000 x g |
| Reduction | 5% SDS, 50 mM DTT, 2 mM EDTA pH 8.5 at 50°C for 20 minutes |
| Sephacryl® S200 column | 50 mM acetate, pH 5.5, 0.1% SDS, 1 mM EDTA |
| Oxidation | Protein: $CuCl_2$, 1:3 (mole/mole) 50 mM phosphate, pH 7.0 |
| Concentration | pH 5.5 |
| Filtration | pH $\leq$ 3, 0.45 μm filter |
| Preparative RP-HPLC | Vydac® C-4 bonded phase silica gel, 2 propanol/acetic acid |
| Precipitation | add one equivalent volume of 0.8 N NaOH into HPLC pool |
| Solubilization | solubilize HPLC precipitate in 0.1 M $Na_2HPO_4$, 1% SDS |
| Sephacryl® S200 column | 50 mM acetate pH 5.5, 0.1% SDS, 1 mM EDTA |
| Desalting--Sephadex G-25 column | pH is raised to 9-9.5; 0.1% sodium laurate as transfer component, 10 mM $Na_2HPO_4$ |
| pH Adjustment | pH lowered to 3 with HCl (1-3 M); sodium laurate precipitates |
| Centrifugation and filtration | To remove precipitated sodium laurate |

FIG.1A

| | |
|---|---|
| Stabilization | 0.1% PEG (4000) monostearate added at pH 3 to 3.2; incubation for 15 minutes |
| Neutralization | pH is raised to 7.0 with NaOH |
| Polyol Addition | 5.0% dextrose |
| Pre-filtration | 0.45 μM |
| Sterile filtration | 0.22 μM |
| Lyophilization (immediate) | |
| Final container product | |

FIG.1B

IL-2 PROCESS

| | |
|---|---|
| Fermentation | |
| Cell concentration | |
| Cell wall and membrane disruption | distilled water |
| Diafiltration | 5 mM EDTA |
| Redisruption | 2 mM EDTA 1% octanol (v/v) |
| Sucrose suspension | 15-35% sucrose (w/w) |
| Centrifugation | 10,000-20,000 x g |
| Paste solubilization | 2% sodium laurate in phosphate buffered saline, pH 9 |
| Centrifugation | 25,000-35,000 x g |
| Reduction | 1-2% sodium laurate, 50 mM DTT, 2 mM EDTA pH 9.2 at 50°C for 20 minutes |
| Sephacryl® S200 column | 20 mM Tris · HCl, pH 9.2, 1-2% sodium laurate, 1 mM EDTA |
| Oxidation | Protein: $CuCl_2$, 1:3 (mole/mole) 20 mM Tris · HCl, pH 9.2 |
| pH Adjustment | pH lowered to 3 |
| Centrifugation and filtration | pH ≤ 3, 0.45 μm filter |
| Preparative RP-HPLC | Vydac® C-4 bonded phase silica gel, 2 propanol/acetic acid |
| Precipitation | add one equivalent volume of 0.8 N NaOH into HPLC pool |
| Solubilization | solubilize HPLC precipitate in 20 mM Tris · HCl, pH 9.2, 1-2% sodium laurate |
| Sephacryl® S200 column | 20 mM Tris · HCl, pH 9.2, 0.1-0.5% sodium laurate, 1 mM EDTA |
| pH Adjustment | Lower pH to 3.0 with HCl; sodium laurate precipitates |
| Centrifugation and filtration | To remove precipitated sodium laurate; 0.22 μM filter |

FIG.2A

| | |
|---|---|
| Stabilization | 0.1% Triton® X305 added to pH 3.0; incubation for 15 minutes |
| Desalting--Sephadex® G-25 column | pH 3.0; run in presence of non-ionic detergent; 20 mM acetate buffer |
| Neutralization | pH is raised to 7.0 with NaOH |
| Polyol Addition | 5.0% Mannitol |
| Pre-filtration | 0.45 μM |
| Sterile filtration | 0.22 μM |
| Lyophilization (immediate) | |
| Final container product | |

FIG.2B

IL-2 PROCESS

| | |
|---|---|
| Fermentation | |
| Cell concentration | |
| Cell wall and membrane disruption | Distilled water |
| Diafiltration | 5 mM EDTA |
| Redisruption | 2 mM EDTA 1% octanol (v/v) |
| Sucrose suspension | 15-35% sucrose (w/w) |
| Centrifugation | 10,000-20,000 x g |
| Paste solubilization | 5% SDS, phosphate buffered saline |
| Centrifugation | 25,000-35,000 x g |
| Reduction | 5% SDS, 50 mM DDT, 2 mM EDTA pH 8.5 at 50°C for 20 minutes |
| Sephacryl® S200 column | 50 mM acetate, pH 5.5, 0.1% SDS, 1 mM EDTA |
| Oxidation | Protein: $CuCl_2$, 1:3 (mole/mole) 50 mM phosphate, pH 7.0 |
| Concentration | pH 5.5 |
| Filtration | pH $\leq$ 3, 0.45 μm filter |
| Preparative RP-HPLC | Vydac® C-4 bonded phase silica gel, 2 propanol/acetic acid |
| Precipitation/centrifugation | Phosphate buffer added to neutralize pH of HPLC pool |
| Solubilization | HPLC precipitate is solubilized with 7 M guanidine in 10 mM citrate buffer at pH 6.5 |
| Diafiltration/precipitation | To reduce guanidine levels |
| Filtration | 0.2 μm filter to remove precipitate |
| Ion exchange chromatography | Pharmacia® Fast Flow CM Sepharose; 10 mM citrate buffer, pH 6.5, 0.04 to 0.5 M NaCl gradient |
| Desalting - Sephadex® G-25 column | Ion exchange pool desalted into 10 mM citrate buffer, pH 6.5 |

FIG.3A

Non-ionic detergent and bulking/ stabilizing agent addition   0.2% Tween® 80 and 1% sucrose added Sterile filtration   0.2 μm filter Lyophilization Final container product

FIG.3B

PHARMACEUTICAL COMPOSITIONS OF RECOMBINANT INTERLEUKIN-2 AND FORMULATION PROCESSES

This application is a continuation-in-part of copending U.S. Ser. No. 923,383 filed Oct. 27, 1986.

FIELD OF THE INVENTION

This invention is in the field of biochemical engineering. More particularly, the invention concerns stable pharmaceutical compositions of biologically active recombinant interleukin-2 (IL-2) protein which is suitable for therapeutic administration to humans. Further, the invention concerns processes for preparing and formulating such IL-2 compositions.

BACKGROUND OF THE INVENTION

Interleukin-2 (IL-2), a lymphokine which is produced by normal peripheral blood lymphocytes and induces proliferation of antigen or mitogen stimulated T cells after exposure to plant lectins, antigens, or other stimuli, was first described by Morgan, D. A., et al., *Science* (1976) 193:1007-1008. Then called T cell growth factor because of its ability to induce proliferation of stimulated T lymphocytes, IL-2 modulates a variety of functions of immune system cells in vitro and in vivo. IL-2 is one of several lymphocyte-produced messenger-regulatory molecules that mediate immunocyte interactions and functions.

IL-2 was initially made by cultivating human peripheral blood lymphocytes (PBL) or other IL-2-producing cell lines. See, for instance, U.S. Pat. No. 4,401,756. Recombinant DNA technology has provided an alternative to PBLs and cell lines for producing IL-2. Taniguchi, T., et al., *Nature* (1983) 302:305-310 and Devos, R., *Nucleic Acids Research* (1983) 11:4307-4323 have reported cloning the human IL-2 gene and expressing it in microorganisms.

Native human IL-2 is an antigen-nonspecific, genetically unrestricted soluble factor produced by erythrocyte rosette positive T cells stimulated with antigens, mitogens and alloantigens. It is a protein with a reported molecular weight in the approximate range of 13,000 to 17,000 daltons (S. Gillis and J. Watson, *J Exp Med* (1980) 159:1709) isoelectric point in the approximate range of pH 6-8.5. Human IL-2 has a number of in vitro and in vivo effects including enhancing the proliferative responses of human peripheral blood mononuclear cells or murine thymocytes, enhancing the immune response in humans and in animals against bacterial, parasitic, fungal, protozoan and viral infections, and supporting the growth of continuous T cell lines.

Human IL-2 has been obtained from genetically engineered *E. coli* as an unglycosylated protein with biological activities equivalent to those of native, glycosylated IL-2. [Taniguchi et al., *Nature*, 302 (5906): 305-310 (Mar. 24, 1983)., Devos et al., *Nuc. Acids Res.*, 11:4307-4323 (1983); Rosenberg et al., *Science*, 223:1412-1415 (1984); Wang et al., *Science*, 224:1431-1433 (1984); and Doyle et al. *J. Biol. Resp. Modifiers*, 4:96-109 (1985)]. Rosenberg and his co-workers have shown that systemic administration of recombinant IL-2 in high doses causes regression of established metastases in mice [Rosenberg et al., *J. Exp. Med.*, 161:1169-1188 (1985)]; and, in conjunction with lymphokine-activated killer cells, in humans [Rosenberg et al., New Eng. J. Med., 313:1485-1492 (1985)].

U.S. Pat. No. 4,518,584 discloses muteins (analogs) of IL-2 in which the cysteine normally occurring at position 125 of the wild-type or native molecule has been replaced with a neutral amino acid, such as serine or alanine. Such muteins possess the biological activity of native IL-2. The patent discloses that for therapeutic or diagnostic applications, such IL-2 muteins may be formulated in nontoxic, nonallergenic, physiologically compatible carrier media such as distilled water, Ringer's solution, Hank's solution, physiological saline, and the like. Administration of the IL-2 analogs to humans or animals may be oral or intraperitoneal or intramuscular or subcutaneous as deemed appropriate by a physician. The amount of IL-2 mutein administered will usually range between about $1 \times 10^4$ and $2 \times 10^8$ units. EP 200,280 (published Oct.12, 1986) discloses muteins of IL-2 whereby the methionine at position 104 has been replaced by a conservative amino acid.

Microbially produced IL-2 is not glycosylated and is produced in a reduced state by microorganisms. When purified and oxidized (cystine form) the microbially produced IL-2s exhibit activity comparable to native human IL-2.

Procedures for purifying native IL-2 from T cells are described by Watson et al., *J Exp Med* (1979) 150:849-861; Gillis et al., *J Immunology* (1980) 124:1954-1962; Mochizuki et al., *J Immun Meth* (1980) 39:185-201; Welte et al., *J Exp Med* (1982) 156:454-464; and European published patent applications 92163 and 94317. In general, these procedures involve precipitating proteins from culture supernatants with ammonium sulfate followed by a chromatographic fractionation.

Commonly owned U.S. Pat. No. 4,569,790 to K. Koths et al. describes a process for recovering IL-2 from an IL-2 producing microorganism whereby the microorganism cell membrane is disrupted, the disruptate is extracted with an aqueous solution of a chaotropic agent such as urea, the IL-2 is solubilized with a surfactant, e.g., sodium dodecyl sulfate (SDS), and the IL-2 is separated in the presence of a reducing agent.

Purification and activity assurance of precipitated heterologous proteins is also described by U.S. Pat. Nos. 4,511,502; 4,511,503; 4,512,922; 4,518,526 and 4,599,127; and EP 114,506.

Commonly owned U.S. Pat. No. 4,604,377 to Fernandes et al. discloses a formulation of a purified microbially produced recombinant IL-2 in which the IL-2 is admixed with a water soluble carrier, such as mannitol, and a sufficient amount of a surface active agent such as SDS or sodium deoxycholate to ensure solubility of the recombinant IL-2 in water at physiological pH.

Many heterologous proteins are precipitated intracellularly in the form of refractile or inclusion bodies which appear as bright spots visible within the enclosure of the cell under a phase contrast microscope at magnifications down to 1000 fold. See e.g., Miller et al., *Science* (1982) 215:687-690; Cheng, *Biochem. Biophys. Res. Comm.*, (1983) 111:104-111; Becker et al., *Biotech. Advs.* (1983) 1:247-261; Kleid et al., ch. 25 in *Developments in Industrial Microbiology*, Vol. 25, p. 317-325 (Society for Industrial Microbiology, Arlington, VA, 1984) and Marston et al., *Bio/Technology* (September, 1984), pp. 800-804.

EP 206,828 (published Dec. 30, 1986) discloses improved methods for recovering and purifying refractile bodies containing recombinant protein.

Wang et al., *J. Parenteral. Drug Assoc.*, 34, 452–462 (1980) provides a review of excipients and pHs for parenteral products used in the United States. A list of solubilizing agents such as detergents and lipids in use for various drugs is provided in Table I thereof and under section II entitled "Solubilizers, Wetting Agents or Emulsifiers" of that table, polyethylene glycol 300, polysorbate 20, 40 and 80, and propylene glycol among others are listed for a variety of pharmaceuticals.

U.S. Pat. No. 4,645,830 discloses IL-2 compositions comprising a solution with human serum albumin, and a reducing compound adjusted to a pH range of 3 to 6.

Japanese Kokai Application 61/293926 (published Dec. 24, 1986) discloses interleukin-2 compositions containing surfactants (Tween ® 20, Tween ® 80, HCO 60, Brij 35, Triton X-100) as stabilizers.

Morikawa et al., *Cancer Res.*, 47:37–41 (Jan. 1, 1987), reports on the use of Pluronic F-127 gel (a polyoxyethylenepolyoxypropylene surface active block copolymer) as a sustained release vehicle for topical administration of recombinant interleukin-2.

Copending, commonly owned, U.S. application Ser. No. 775,751, filed Sept. 13, 1985 entitled "An Improved Formulation for Lipophilic Proteins" outlines a high pH and a low pH process for recovering and purifying lipophilic recombinant proteins such as HIFN-and $\beta$ and interleukin-2 from host strains to yield a protein preparation which may be formulated into a stable pharmaceutical composition. Said composition carrying a therapeutically effective amount of the biologically active lipophilic protein dissolved in a non-toxic, inert, therapeutically compatible aqueous-based carrier medium at a pH of 6.8 to 7.8 also contains a stabilizer for the protein, such as human serum albumin, human serum albumin and dextrose, and human plasma protein fraction.

EP 217,645 (published Apr. 8, 1987) discloses pharmaceutical compositions containing IFN-$\beta$ or interleukin-2 dissolved in a stable carrier medium at pH 7.0 to 8.0 stabilized with sodium laurate.

WO 87/00056 (published Feb. 15, 1987) discloses pharmaceutical compositions wherein recombinant IFN-$\beta$, IL-2 or an immunotoxin is dissolved in an aqueous carrier medium without the presence of a solubilizing agent. Such unconjugated proteins are insoluble in water at pH 6–8 without a solubilizing agent. The protein is solubilized by selectively conjugating it via a coupling agent to a water-soluble polymer selected from polyethylene glycol homopolymers or polyoxyethylated polyols.

There remains a need in the art for formulations of biologically active, recombinant interleukin-2 that are pure enough for clinical administration but substantially or totally free of residual strong detergents or chaotropes, such as SDS, used in the extraction and purification processes. Further, there is a need for formulations that provide alternatives to those containing non-IL-2 protein, such as those containing albumin.

Further, alternative processes for preparing formulations containing biologically active, recombinant interleukin-2 which avoid very high pH ranges are desirable. The instant invention meets such needs.

SUMMARY OF THE INVENTION

The present invention provides stable pharmaceutical compositions of matter suitable for parenteral administration to animals or humans comprising a therapeutically effective amount of a recombinant interleukin-2 (IL-2) protein dissolved in an inert carrier medium comprising as a stabilizer, an effective amount of one or more biocompatible non-ionic polymeric detergents.

Another aspect of this invention concerns methods of screening for biocompatible non-ionic polymeric detergents or combinations of biocompatible non-ionic polymeric detergents for inclusion as solubilizers in the pharmaceutical compositions of recombinant IL-2 (IL-2) described herein. One such method comprises the steps of:

a. passing extracted, partially purified IL-2 in sodium dodecyl sulfate through a desalting column equilibrated in a fatty acid salt having from about 10 to about 13 carbons in an elution buffer at a concentration from about 5 to about 20 mM and at a pH from about 8.5 to about 9.5 to obtain an eluate of IL-2;

b. lowering the pH of the eluate to a range of about 2 to about 4;

c. centrifuging and filtering to remove the precipitated fatty acid salt;

d. adding 0.001% to 5% by volume of one or more biocompatible non-ionic polymeric detergents to the centrifugate., e. adjusting the pH of the centrifugate to 3.0 to 9.5;

f. allowing the centrifugate to stand for about 24 hours at the pH range of 3.0 to 9.5; and g. observing visually and by UV scan after 24 hours whether the IL-2 remains in solution. Another such method concerns screening of said detergents for inclusion as solubilizer/stabilizers in pharmaceutical compositions of IL-2 wherein the IL-2 has been extracted from a microbial host transformed to produce said IL-2 and purified by a process wherein the IL-2 is denatured and then renatured by an effective amount of a chaotropic agent, comprising the steps of adding 0.001% to 5% by volume or weight of one or more biocompatible non-ionic polymeric detergents to the extracted and purified IL-2 and observing visually after from about 4 to about 24 hours whether the IL-2 remains in solution at room temperature.

A still further aspect of this invention concerns methods of preparing stable pharmaceutical compositions of recombinant interleukin-2 (IL-2) protein. One such method comprises the steps of:

(a) extracting the IL-2 from the disruptate of a host organism transformed to produce the IL-2 protein;

(b) purifying the IL-2 protein using, as the last step of purification, a desalting step at a pH range of 8.5 to 10, wherein a fatty acid salt having from about 10 to about 13 carbons is employed to obtain a desalted pool;

(c) lowering the pH of the desalted pool to about 2 to about 4;

(d) centrifuging and filtering the desalted pool to remove the fatty acid salt precipitate;

(e) mixing the centrifuged purified and filtered interleukin-2 in an inert carrier medium with an effective amount of one or more non-ionic biocompatible polymeric detergents to obtain a formulation;

(f) adjusting the pH of the formulation to between about 3.0 and 9.5;

(g) adding to the formulation an effective amount of a bulking agent; and (h) immediately lyophilizing the formulation. Another method of preparing said compositions comprises the steps of:

(a') isolating refractile bodies containing IL-2 from a host organism transformed to produce said IL-2;

(b') solubilizing said refractile bodies by employing sodium laurate;

(c') extracting and purifying said IL-2 from the solubilized refractile material employing sodium laurate as the primary solubilizing agent;

(d') lowering the pH of the purified IL-2 to a pH from about 3 to about 3.5;

(e') centrifuging and filtering the purified IL-2 to remove the precipitated sodium laurate;

(f') adding to the centrifugate containing the IL-2 an effective amount of one or more biocompatible non-ionic polymeric detergents;

(g') desalting the centrifugate at a pH of from about 2 to abour 4;

(h') adjusting the pH of the desalted pool to neutral pH;

(i') adding to the desalted pool an effective amount of a bulking/stabilizing agent to obtain a formulation; and (j') immediately lyophilizing the formulation.

BRIEF DESCRIPTION OF THE DRAWINGS

FIG. 1 sequentially illustrates the steps of a preferred embodiment of the instant invention for extracting, purifying and formulating microbially produced IL-2. In this flow chart SDS is employed as the primary solubilizing agent during extraction and purification, and sodium laurate is employed as a transfer component during desalting on a G-25 column to remove the SDS. PEG (4000) monostearate (0.1%; wt/v) is stabilizer and dextrose (5%; wt/v) is the bulking agent.

FIG. 2 sequentially illustrates a further preferred embodiment of the instant invention for extracting, purifying and formulating microbially produced IL-2 wherein sodium laurate, rather than SDS, is employed as the primary solubilizing agent. Triton ® X305 (0.1%; v/v) is the stabilizer in the formulation, and mannitol (5.0%; wt/v) is bulking agent.

FIG. 3 sequentially illustrates a preferred embodiment of the process illustrated in FIG. 4 for extracting, purifying and formulating microbially produced IL-2 wherein the process comprises denaturing oxidized, purified IL-2 by placing the IL-2 in a solution of a chaotropic agent (7M guanidine in 10 mM citrate buffer), removing solids from the solution, thereafter renaturing the IL-2 by removing the chaotropic agent and formulating the IL-2 with the non-ionic biocompatible polymeric detergent Tween ® 80 (0.2%; v/v) and sucrose (1%; wt/v) as a bulking agent.

DETAILED DESCRIPTION OF THE PREFERRED EMBODIMENTS

Figure 4:
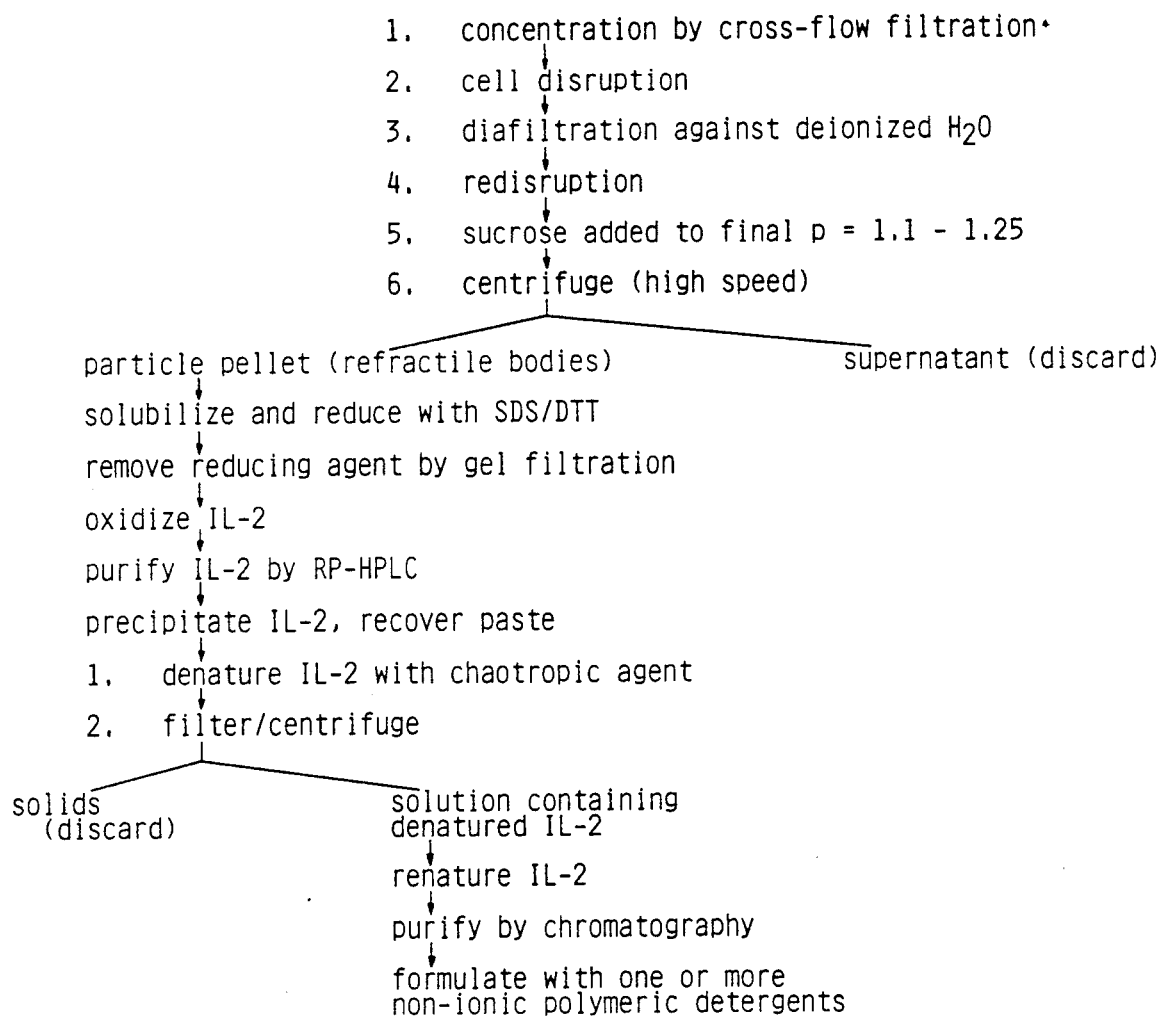
FIG. 4 is a flow diagram illustrating a preferred process of extracting, purifying and formulating microbially produced IL-2 according to this invention.

This invention provides for highly stable pharmaceutical compositions of matter suitable for parenteral administration to animals or humans comprising a therapeutically effective amount of a recombinant IL-2 (IL-2) protein dissolved in an inert carrier medium comprising one or more biocompatible non-ionic polymeric detergents.

The term "recombinant interleukin-2," designated as IL-2, preferably human IL-2, refers to interleukin-2 having biological activity comparable to native IL-2 prepared by recombinant DNA techniques as described, e.g., by Taniguchi et al., Nature, 302:305–310 (1983) and Devos, *Nucleic Acids Research*, 11:4307–4323 (1983). In general, the gene coding for IL-2 is excised from its native plasmid and inserted into a cloning vector to be cloned and then into an expression vector, which is used to transform a host organism, preferably a microorganism, and most preferably *E. coli*. The host organism expresses the foreign gene to produce IL-2 under expression conditions.

More preferably the IL-2 is a mutein as described in U.S. Pat. No. 4,518,584, in which the cysteine normally occurring at position 125 of the wild-type or native molecule has been replaced by a neutral amino acid such as serine or alanine. Alternatively or conjunctively, the IL-2 mutein may be one as described in EP 200,280, published Dec. 10, 1986, the disclosure of which is incorporated herein by reference, in which the methionine normally occurring at position 104 of the wild-type or native molecule has been replaced by a neutral amino acid such as alanine.

Preferably, the IL-2 is a protein produced by a microorganism or by yeast which has been transformed with the human cDNA sequence of IL-2 that encodes a protein with an amino acid sequence at least substantially identical to the amino acid sequence of native human IL-2, including the disulfide bond of the cysteines at positions 58 and 105, and has biological activity which is common to native human IL-2. Substantial identity of amino acid sequences means the sequences are identical or differ by one or more amino acid alterations (deletions, additions, substitutions) which do not cause an adverse functional dissimilarity between the synthetic protein and native human IL-2. Examples of such recombinant IL-2 proteins with such properties include those described by Taniguchi et al., supra; Devos, supra; European Pat. Publication Nos. 91,539; 88,195; 109,748 and 200,280; and U.S. Pat. No. 4,518,584, supra; N-terminal deleted muteins of IL-2 wherein the first five (1–5) amino acids are deleted; and bovine IL-2 as described by Cerretti et al., PNAS, 83:3223–3227 (1986).

The precise chemical structure of the IL-2 protein herein will depend on a number of factors. As ionizable amino and carboxyl groups are present in the molecule, a particular IL-2 protein may be obtained as an acidic or basic salt, or in neutral form. All such preparations that retain their bioactivity when placed in suitable environmental conditions are included in the definition of IL-2 proteins herein. Further, the primary amino acid sequence of the IL-2 protein may be augmented by derivatization using sugar moieties (glycosylated) or by other supplementary molecules such as lipids, phosphate, acetyl groups and the like, more commonly by conjugation with saccharides. Certain aspects of such augmentation are accomplished through post-translational processing systems of the producing host; other such modifications may be introduced in vitro. In any event, such modifications are included in the definition of IL-2 protein herein so long as the bioactivity of the protein is not destroyed. It is expected, of course, that such modifications may quantitatively or qualitatively affect the bioactivity by either enhancing or diminishing the activity of the IL-2 protein in the various assays.

The recombinant IL-2s particularly preferred herein are those biologically active muteins (analogs) in which amino acid residues not essential to biological activity have been deliberately deleted in some instances (as indicated below) or replaced with a conservative amino acid. More specifically, preferred recombinant IL-2s include those wherein the cysteine residue at position 125 is replaced with another amino acid, preferably neutral or conservative, to eliminate sites for intermolecular crosslinking or incorrect intramolecular disulfide bond formation; those wherein the methionine residue at position 104 is replaced with another amino acid to reduce heterogeneity; those wherein the N-terminal alanine residue of the native counterpart is eliminated; those wherein the first five amino acids are deleted., those wherein the N-terminal alanine residue is eliminated and the cysteine at position 125 is replaced by a neutral amino acid; and those wherein the N-terminal alanine residue is eliminated, and the cysteine at position 125 as well as the methionine at position 104 are replaced by neutral or conservative amino acids. More particularly, preferred recombinant IL-2 muteins in the formulations of this invention are those wherein the cysteine residue at amino acid position 125 of the native counterpart is replaced by a serine residue (designated IL-2$_{ser125}$) or alanine residue (designated IL-2$_{ala125}$); those wherein the N-terminal alanine residue of the native counterpart is eliminated (designated des-alanyl$_1$-IL-2); those wherein the N-terminal alanine residue is eliminated and the cysteine at position 125 is replaced by serine (designated des-alanyl-IL-2$_{ser125}$); those wherein the methionine at position 104 is replaced by alanine (designated IL-2$_{ala104}$); and those wherein the N-terminal alanine eliminated, the methionine at position 104 is replaced with alanine and wherein the cysteine at position 125 is replaced with serine (designated des-alanyl$_1$-IL-2$_{ala104, ser125}$).

Further, individual amino acid residues in the chain may be modified by oxidation, reduction, or other derivatization, and the protein may be cleaved to obtain fragments which retain activity. Such alterations which do not destroy activity do not remove the protein sequence from the definition.

The biocompatible non-ionic polymeric detergents of the pharmaceutical compositions of this invention are non-toxic surface active agents used in the food, pharmaceutical, and cosmetic industries and have molecular weights in the range of approximately 100 to 250,000, preferably about 500 to 100,000, and most preferably about 1,000 to 5,000 daltons.

Preferred biocompatible non-ionic polymeric detergents employed as stabilizers in the formulations of this invention are selected from the group comprising octylphenoxy polyethoxy ethanol compounds, polyethylene glycol monostearate compounds, and polyoxyethylene sorbitan fatty acid esters.

Such preferred biocompatible, non-ionic polymeric detergents ted from the group comprising octylphenoxy polyethoxy ethanol compounds having the formula

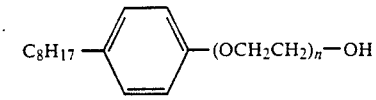

wherein n is an integer from about 15 to about 50, more preferably wherein n is an integer from about 25 to 45, still more preferably wherein n is an integer from about 30 to about 40, and still more preferably wherein n is either 30 or 40;

polyethylene glycol monostearate compounds having the formula

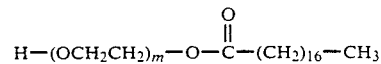

wherein m is an integer from about 10 to about 200; more preferably wherein m is an integer from about 50 to about 150; still more preferably wherein m is an integer from about 75 to about 125; and still more preferably wherein m is an integer from about 85 to about 95 and polyoxyethylene sorbitan fatty acid esters (polysorbate compound) having the formula

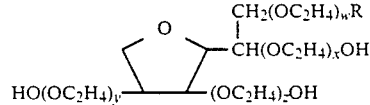

wherein the sum of the integers w, x, y and z equals 20 and R is a fatty acid having from about 10 to about 20 carbon atoms; more preferably wherein R is a fatty acid having from about 12 to about 18 carbons; still more preferably wherein R is either lauric acid or oleic acid; and still more preferably wherein R is oleic acid.

Preferred commercially available octylphenoxy polyethoxy ethanol compounds described immediately above as the most preferred species are known by the tradename Triton ® X305 wherein n is 30, and by Triton ® X405 wherein n is 40. Preferred polyethylene glycol monostearate compounds are those wherein m is from about 85 to about 95; more preferred is a polyethylene glycol monostearate compound having a molecular weight of about 4000 which is known as Mapeg 4000 (MS), PEG (4000) monostearate or MaPEG. Highly preferred polysorbate compounds described above include polysorbate 20 and polysorbate 80 compounds, which are respectively commercially available and known by various trade name such as, Tween ® 20 (wherein R is lauric acid) and Tween ® 80 or Durfax ® 80 (wherein R is oleic acid); polysorbate 80 compounds are preferred stabilizer/solubilizers of this invention and Tween ® 80 is a preferred commercial source therefor.

The ampiphilic nature of non-ionic surfactants is often expressed in terms of the balance between the hydrophobic and hydrophilic portions of the molecule. An empirical scale of hydrophile-lipophile balance numbers (HLB) has been devised. An HLB number is a value extending from 1 to approximately 50, which indicates the extent of hydrophilicity or lipophilicity of a surface-active agent. The more hydrophilic surfactants have high HLB numbers (in excess of 10), whereas surfactants with HLB numbers from 1 to 10 are considered to be lipophilic.

Preferred biocompatible non-ionic polymeric detergents in the formulations of this invention have hydrophile-lipophile (HLB) numbers in the range of from about 10 to about 40, more preferably from about 15 to about 30, and still more preferably from about 15 to about 20.

Triton ® X305 has an HLB of about 17.3, and Triton ® X405 has an HLB of about 17.9. Mapeg 4000 (MS) has an HLB of about 18.7. Tween ® 80 has an HLB of about 15, and Durfax ® 80 has an HLB of about 17.3. Tween ® 20 has an HLB of about 16.7.

The above-noted biocompatible non-ionic polymeric detergents are commercially available from the following companies:

| | |
|---|---|
| Triton ® X305 and Triton ® X405 Rohm and Haas Delaware Valley Inc. 5000 Richmond Street Philadelphia, Pennsylvania 19105 | Tween ® 20 and Tween ® 80 ICI Americas Inc. New Murphy Road & Concord Pike Wilmington, Delaware 19897 |
| Mapeg 4000 (MS) Mazur Chemicals, Inc. 3938 Porett Drive Gurnee, Illinois 60031. | Durfax ® 80 SCI Durkee Foods Huntington Bldg. 925 Euclid Ave. Cleveland, Ohio 44115 |

Further biocompatible non-ionic polymeric detergents having the above-noted parameters can be found in editions of McCutcheon's Emulsifiers & Detergents published by the McCutcheon Division of MC Publishing Co., 175 Rock Road, Glen Rock, NJ (USA). Biodegradable non-ionic polymeric detergents suitable as solubilizers of purified IL-2 can be selected for the formulations of this invention by the screening procedures outlined below.

The concentration ranges (volume/volume for all the detergents except for MaPEG for which the concentration is expressed in terms of weight/volume) of the biocompatible non-ionic polymeric detergents in the pharmaceutical compositions of this invention are preferably from about 0.001% to about 5%, more preferably from about 0.005% to about 3%, and still more preferably from about 0.01% to about 1%.

If a combination of two non-ionic detergents is used to solubilize IL-2 in the pharmaceutical compositions of this invention, it is preferred that they be in a volume/volume concentration ratio of about 0.01%:0.75%, more preferably about 0.025%:0.5%, and still more preferably about 0.05%:0.2%.

It is preferred that the concentration of the IL-2 in the pharmaceutical compositions of this invention be in the range of from about 0.05 mg/ml (of the carrier medium) to about 10 mg/ml, more preferably about 0.1 mg/ml to about 5 mg/ml, and still more preferably about 0.1 mg/ml to about 2 mg/ml. Representative dosage amounts of IL-2 in the pharmaceutical compositions of this invention in the final container vial are: a high dosage amount of about 1 mg/ml; a normal dosage amount of about 0.25 mg/ml; and a low dosage amount of about 0.125 mg/ml.

The particular biocompatible polymeric non-ionic detergents employed and the concentrations thereof depend mainly on the process used to extract and purify the microbially produced IL-2, the particular IL-2 protein or analog to be formulated, the concentration of the IL-2, and the pH of the formulation. The optimal concentration of the non-ionic detergent depends upon the pH of the formulation. In general, the lower the pH of the formulation, the lower the concentration of the non-ionic detergent or detergents that is necessary to stabilize the recombinant IL-2 protein therein. Thus, it is preferred that when a lower pH is selected for a formulation of this invention, for example, for a pH of about 3 to about 4, the non-ionic detergent is at the lower end of the concentration range, for example, from about 0.005% to about 0.02%; whereas when a higher pH is selected for the formulations of this invention, for example, a pH range from about 6 to about 7, a higher concentration of the non-ionic detergent is preferably employed, for example, from about 0.05% to about 0.2%.

Further, in general, higher concentrations of IL-2 in the pharmaceutical compositions of this invention require higher concentrations of the one or more biocompatible, non-ionic polymeric detergents of this invention; whereas lower dosage formulations of IL-2 require lower concentrations of the non-ionic detergents to stabilize and solubilize the IL-2 successfully.

The term "primary solubilizing agent" herein is defined to mean a solubilizing agent, preferably, a detergent and/or chaotrope which is used to solubilize the IL-2 from the refractile bodies in the abbreviated or expanded front-end processes of purifying rIFN-β as described infra. The primary solubilizing agent is preferably then relied upon to maintain the IL-2 in solution throughout the purification process up to its removal, preferably by desalting, and formulation with the non-ionic detergents of this invention. For example, a primary solubilizing agent is exemplified by sodium dodecyl sulfate (SDS) in FIG. 1 and by sodium laurate in FIG. 2.

The term "chaotropic agent" or "chaotrope" herein is defined to mean a compound or compounds which, in aqueous solution and in a suitable concentration, are capable of denaturing IL-2. Correlatively, the term "strongly denaturing concentrations" refers to a solution of a chaotropic agent which will effectively "unfold" or denature IL-2.

Guanidine salts (e.g., the hydrochloride) and alkali metal thiocyanates (e.g., sodium thiocyanate) at concentrations in the range of about 4 to 9 M, preferably about 6 to 9 M, and more preferably about 7 M, are examples of chaotropic agent solutions that will dissolve and denature IL-2. An alternative and less preferred chaotropic agent is aqueous urea, 4–8 M.

The term "oxidized" as used to characterize IL-2 and processes for making same intends IL-2 in which the disulfide bonding that occurs in native IL-2 is present and processes which promote such bonding without effecting oxidation that does not occur in native IL-2.

As used herein the term "transformed" in describing host microorganism cell cultures denotes a microorganism that has been genetically engineered to produce IL-2 that possesses the activity of native IL-2. Bacteria are preferred microorganisms for producing IL-2. *E. coli* is particularly preferred.

As used herein, the term "solubilizer" as applied to the recombinant IL-2 formulations refers to essentially non-toxic, non-immunogenic compositions which act not only to stabilize the diafiltered or desalted IL-2, preferably desalted IL-2, against denaturation and loss of biological activity, but also to solubilize the lipophilic protein in an aqueous medium so that the pharmaceutical formulation constitutes an aqueous solution of diafiltered or desalted, preferably desalted, IL-2 protein at pH 3.0 to 9.5, preferably 4–8, more preferably 5 to 7.5, and still more preferably from about 6 to about 6.5, from which the protein will not precipitate. The solubilizer compositions of this invention are one or more biocompatible, non-ionic polymeric detergents characterized as described herein.

As used herein, the term "physiological pH" refers to a pH which is pharmaceutically acceptable to mammals.

Neutral pH is herein considered to be a pH in the range of from about 6 to about 8.

Microbially produced IL-2 is not glycosylated and is produced in a denatured state. It is insoluble and, when expressed at high levels, it precipitates intracellularly in the form of "refractile" or "inclusion" bodies which appear as bright spots visible within the enclosure of the cell under a phase contrast microscope at magnification down to 1000 fold.

Recombinant IL-2 to be formulated according to this invention can be extracted and purified from transformed microorganisms by any, process known in the art which results in the extracted IL-2 being purified to a pharmaceutically acceptable level. However, it is preferred that the process used to extract and purify the microbially produced IL-2 comprise the steps of treating the IL-2 with a denaturing concentration of a chaotropic agent and then treating the denatured IL-2 with a renaturing concentration of a chaotropic agent. When such a process is used, the extracted and purified IL-2 has improved stability and water solubility characteristics, in that it is more soluble and stable in a pH range of from about 5 to about 8, than is IL-2 extracted and purified by methods cited in the Background supra or by the procedures of Example 1 as outlined in FIG. 1. Thus, when the IL-2 is extracted and purified according to the preferred processes herein described wherein it is denatured and then renatured with appropriate concentrations of a chaotropic agent, the stabilizers of this invention act more to stabilize the purified IL-2 than to solubilize it, in that the IL-2 in a renatured form is essentially soluble at a pH range of about 5 to about 8; whereas IL-2 expressed in *E. coli* and extracted and purified according to methods such as that outlined in FIG. 1, is in a denatured form and is not soluble and stable at such a pH range, and therefore, the stabilizers of this invention act both to solubilize and stabilize such IL-2 compositions.

Further, the IL-2 extracted and purified according to such preferred processes can be successfully stabilized by a wider variety of biocompatible non-ionic polymeric detergents. For example, IL-2 processed according to Example 1 is not readily solubilized and stabilized with Durfax® 80 or Tween® 20, whereas the IL-2 extracted and purified according to Example 9, wherein the IL-2 is denatured and then renatured in the presence of respectively decreasing concentrations of the chaotropic agent guanidine hydrochloride, is successfully stabilized with Tween® 80 and Tween® 20.

Expecially preferred, according to this invention, are processes for extracting and purifying IL-2 from transformed microorganisms which comprise the steps of denaturing and then renaturing the IL-2 in the presence of a chaotropic agent, which processes are disclosed in U.S Serial 0 and 048,408, which were both filed on May 11, 1987 both now abandoned are both entitled "Improved Process for Recovering Microbially Produced Interleukin-2" and are both herein incorporated by reference.

U.S. Ser. No. 048,405 discloses a process for recovering IL-2 from transformed microorganisms containing the IL-2 wherein the IL-2 is separated from the bulk of the cellular components of the microorganisms, solubilized in a reduced form, oxidized, and thereafter purified to clinically acceptable purity and endotoxin levels. Central to said process are the steps of denaturing the oxidized, purified IL-2 by placing the IL-2 in a solution of a chaotropic agent, removing solids from the solution, and thereafter renaturing the IL-2 from the solution. FIGS. 3 and 4 graphically illustrate such a process, and Example 9 is representative thereof.

Figure 5:
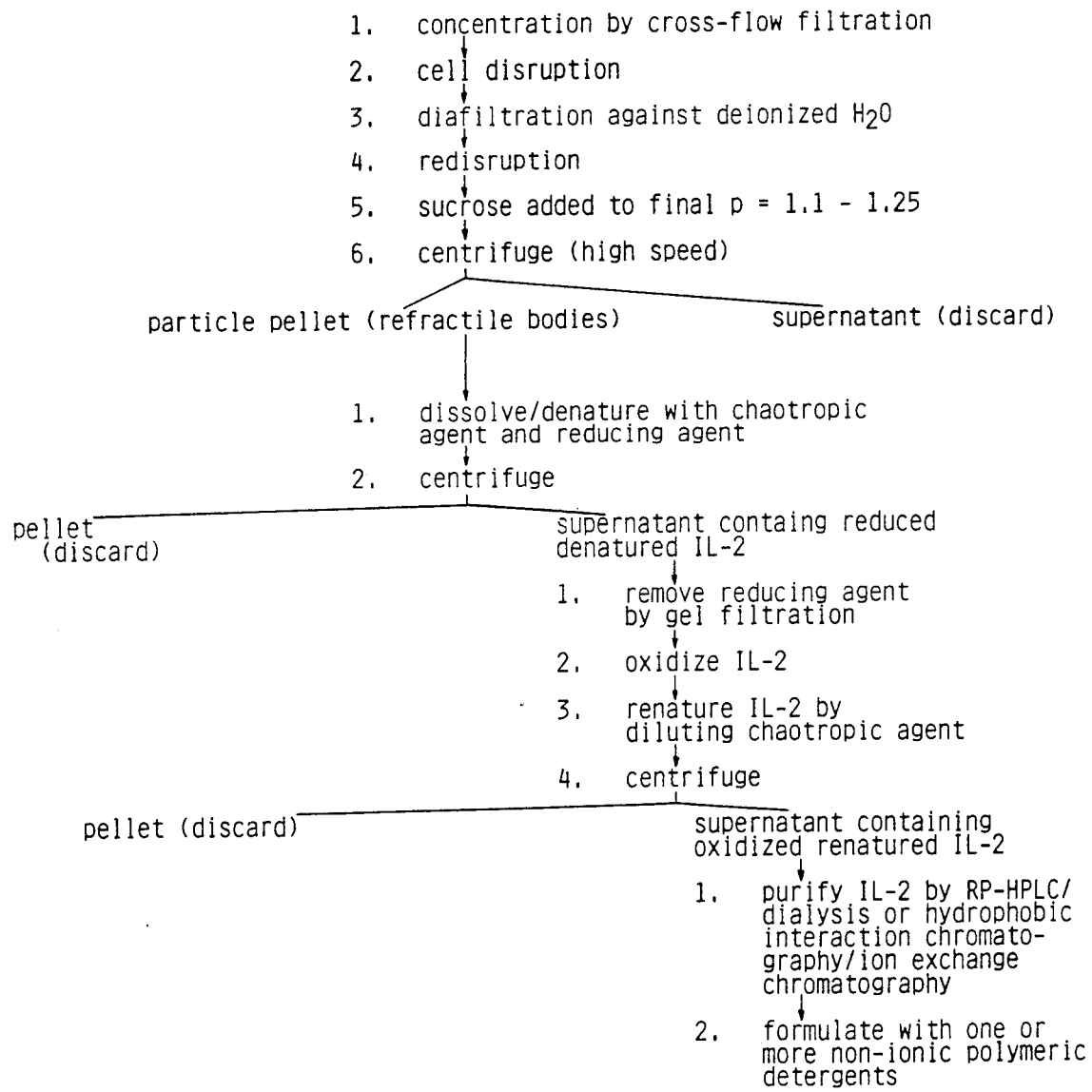
FIG. 5 is a flow diagram illustrating a preferred process of this invention for extracting, purifying and formulating microbially produced IL-2 wherein the IL-2 is separated from a cellular disruptate in the form of a refractile body, dissolved with a chaotropic agent and oxidized and renatured in separate steps followed by purification to a clinically acceptable level and formulation with one or more biocompatible non-ionic polymeric detergents.

U.S. Ser. No. 048,408, filed May 11, 1987 discloses a process in which microbially produced IL-2 is separated from a cellular disruptate in the form of a refractile body, dissolved with a chaotropic agent and oxidized and renatured in separate steps followed by purification to a clinically acceptable level. FIG. 5 illustrates the steps of such a process.

More specifically, the process disclosed in U.S. Ser. No. 048,408 for recovering purified soluble IL-2 from a transformed microorganism containing the IL-2 comprises the following steps:

(a) disrupting the cell wall and membrane of the microorganism;

(b) separating water-insoluble material from the disruptate;

(c) mixing the insoluble material of step (b) at a pH of about 7 to about 9 with an aqueous solution of a reducing agent and a strongly denaturing concentration of a chaotropic agent whereby the IL-2 in the insoluble material is dissolved;

(d) separating the IL-2 containing solution of step (c) from the undissolved portion of the insoluble material;

(e) removing the reducing agent from the separated IL-2-containing solution;

(f) oxidizing the IL-2 in the solution whereby the natural disulfide bridge of IL-2 is formed;

(g) after the oxidation step (f) is complete, diluting the solution to reduce the concentration of chaotropic agent in the solution to a level at which the oxidized IL-2 is renatured and a precipitate forms;

(h) separating the precipitate from the solution to provide a supernatant;

(i) purifying the oxidized, renatured IL-2 in the supernatant by reverse-phase high performance liquid chromatography followed by removal of residual chaotropic agent and separation of any precipitate formed by said removal, or by hydrophobic interaction chromatography followed by ion exchange chromatography; and (j) recovering a purified oxidized, soluble heterologous human IL-2.

The pharmaceutical compositions of this invention can be in liquid form or lyophilized. Considered first in detail herein are liquid formulations.

The liquid formulations are preferably frozen or stabilized and maintained at a temperature range of from about −70° C. to about +10° C. The frozen formulations are preferably maintained at a temperature range of from about −70° C. to about −20° C., whereas the stabilized liquid formulations are preferably maintained at a normal refrigeration range, preferably from about +2° C. to about +8° C.

The liquid formulations of this invention comprise:
(1) microbially produced, IL-2;
(2) one or more biocompatible non-ionic detergents; and
(3) a small amount of buffer that maintains the formulations at a physiologically acceptable pH range.

The buffer selected to maintain the liquid formulations at a physiologically acceptable pH range is preferably at a concentration from about 5 to about 50 mM, more preferably about 10 to about 20 mM, and still more preferably about 10 mM.

The liquid formulations can further comprise an additional stabilizing agent, preferably one or more carbohydrates, and more preferably one or more sugars. Preferred stabilizing agents are selected from the group comprising sucrose, fructose, dextrose, maltose, glucose, dextran, mannitol, sorbitol, inositol, galactitol, xylitol, lactose, and trehalose, preferably sucrose, dextrose and mannitol, and more preferably dextrose and sucrose. Non-carbohydrate stabilizing agents can include, for example, human serum albumin (HSA) and bovine serum albumin (BSA). Such stabilizing agents are preferably in a concentration (weight/volume) range of from about 0.025% to about 10%, preferably from about 0.05% to about 7%, and more preferably from about 0.1% to about 5%.

The liquid formulations can further comprise a small amount of a preservative to enhance chemical stability and an anti-oxidant to counteract the effects of any peroxides potentially present in the commercial non-ionic detergent preparations.

The lyophilized formulations of this invention comprise:
(1) microbially produced IL-2;
(2) one or more biocompatible non-ionic polymeric detergents;
(3) a small amount of a buffer that provides a physiologically acceptable pH range upon reconstitution; and
(4) a bulking agent.

The liquid formulations of this invention were noted above to include optionally one or more carbohydrate or non-carbohydrate stabilizers. The lyophilized formulations, however, require an agent which not only can provide some stabilizing effect to the pharmaceutical compositions but also provide bulk to the lyophilized product, and such agents are herein termed bulking agents. Such bulking agents can be selected from the carbohydrate and non-carbohydrate stabilizing agents noted above for liquid formulations and can be at similar preferred concentration ranges.

Preferably, the bulking agents and buffers are selected for lyophilized formulations of this invention according to the method by which the IL-2 was extracted and purified, in that the choice of such method determines whether the IL-2 to be formulated requires an amorphous or crystalline environment for most successful lyophilization. [MacKensie, *Bull. Parenteral Drug Assoc.*, 20(4):101–129 (1966) and Mackensie, *Develop. Biol. Standard.*, 36:51–67 (S. Karger, Basel 1977) discuss in detail amorphous and crystalline environments in relation to lyophilization procedures. The disclosures of these two references are herein incorporated by reference.] For example, it is preferred that IL-2 extracted and purified according to the preferred processes outlined above wherein the IL-2 is denatured and then renatured in the presence of a chaotropic agent, more preferably according to the procedures outlined in FIGS. 3 to 5, be lyophilized in an amorphous environment; and that the IL-2 extracted and purified according to the procedures outlined in FIG. 1, be lyophilized in a crystalline environment.

Preferred bulking agents for providing an amorphous environment comprise polyol sugars, preferably, sucrose, dextrose, lactose, maltose, glucose, trehalose, fructose, and more preferably sucrose. The most preferred buffer for providing an amorphous environment for lyophilization is citrate, which provides a pH range preferably from about 3.0 to about 7.0, more preferably from about 3.5 to about 6.5. Still more preferably, wherein higher concentrations of the non-ionic detergent stabilizers of this invention are selected, the preferred pH range is from about 6 to about 7, more preferably from about 6 to about 6.5; and wherein lower concentrations of the non-ionic detergents are selected, the preferred pH range is from about 3 to about 4, more preferably about pH 3.5.

For providing a crystalline environment for lyophilization, mannitol is a preferred bulking agent, and glycine and phosphate, more preferably phosphate, are preferred buffers.

Further, although less preferred, combinations of a bulking agent for an amorphous lyophilization environment and a bulking agent for a crystalline lyophilization environment can also in certain ratios provide the requisite conditions for successful lyophilization. For example, a combination of a crystalline bulking agent, preferably mannitol, and an amorphous bulking agent, preferably sucrose, in a volume ratio of from about 20/1 to about 1/1 can provide an adequate lyophilization environment for IL-2 which requires an amorphous environment wherein a crystalline plug is formed in the final container vial.

The concentration range for the buffers preferred for the lyophilized formulations of this invention are the same as the ranges noted above for buffers in the liquid formulations.

The lyophilized formulations further can comprise an antioxidant.

Preferred examples of lyophilized formulations of this invention wherein the IL-2 was extracted and purified according to the procedure comprising the steps of denaturing and renaturing the IL-2 in the presence of a chaotropic agent, more preferably according to the procedures outlined in FIGS. 4 and 5, are as follows:
1.0 mg/ml IL-2 (preferably des-ala$_1$-IL-2);
0.2% (vol/vol) Tween ® 80;
1.0% (wt/vol) sucrose;
10 mM citrate buffer;
at pH 6.5; and
0.02% (vol/vol) Tween ® 80;
1.0% (wt/vol) sucrose;
10 mM citric acid;
at pH 3.5.

Many of the methods used for the recovery of recombinant proteins, such as bacterially produced IL-2, utilize SDS or similar surfactants for the solubilization and isolation of the protein from the cellular material and subsequent acid precipitation to obtain the protein. By further purification techniques carried out at or near neutral pH, the SDS levels in the final protein preparations are reduced to about 0.1%. Further removal by diafiltration or desalting techniques in the 3–8 pH range does not follow first-order kinetics due to protein-SDS interactions which significantly affect the kinetics of SDS removal. It was found that SDS removal from recombinant proteins promotes protein-protein interactions at the range of 3–8 that result in aggregation or precipitation of the protein and consequent loss of activity.

One solution to the problem of such aggregation and precipitation during SDS removal is described in U.S. Pat. No. 4,462,940. That procedure uses a high pH range (10.5 to 12.5) during diafiltration and desalting.

The formulations of this invention are preferably prepared by processes designed to avoid conditions of strong alkalinity. Preferred processes described above for extracting and purifying IL-2, wherein the IL-2 is denatured and renatured in the presence of a chaotropic agent, avoid high pH ranges and allow for the formulation of the IL-2 at or about neutral pH or at lower pH ranges. When such preferred, processes are not used, and instead a process such as that exemplified in FIG. 1 is used, it is preferred as another aspect of this invention, to avoid high pH diafiltration or desalting conditions, to employ a milder detergent or chaotrope as a transfer component during diafiltration or desalting, preferably desalting, to replace stronger solubilizing agents such as SDS used in the extraction and purification of the recombinant IL-2 from the host microorganism. Such milder detergent/chaotropes used as transfer components allow for diafiltration or desalting of the IL-2 to occur at a lower pH range, for example, from pH 8.5 to 10.0, preferably 9–9.5, and more preferably, 9–9.2. Examples of such detergent/chaotropes for use as transfer components include fatty acid salts having carbon chains of from about 10 to about 13 carbons, preferably 11 to 12 carbons, and more preferably 12 carbons. It is preferred that the fatty acid salt be a laurate salt and most preferred that such laurate salt be sodium laurate.

The concentration range (weight/volume) of said transfer component in a preferably low ionic strength elution buffer is from about 0.05% to about 2%, preferably 0.1% to 1%. Preferred low ionic strength elution buffers include Tris HCl, citrate, borate, sodium pyrophosphate and sodium phosphate at concentrations of preferably 5 to 20 mM, and more preferably 10 to 15 mM. Tris.HCl and disodium phosphate are preferred buffers.

In addition to the fatty acid salts, a number of other detergent/chaotropes can be used as transfer components in this process, for example, urea (5–7 molar, preferably 6M), or more preferably guanidine hydrochloride (5–7 molar, preferably 6 M).

The pH of the thus purified IL-2 pool which has been diafiltered or desalted, preferably desalted, by said process employing a transfer component, is then adjusted to a pH of about 2 to about 4, preferably 3 to 4, and more preferably about 3.5, at which point if the transfer component is sodium laurate it will precipitate from the solution. The precipitated sodium laurate is then removed by centrifugation and filtration or by other means known to those skilled in the art. If the transfer component is other than sodium laurate, for example, urea or guanidine, it will not precipitate at pH 3 and needs to be removed earlier in the process by desalting.

In such a process using a transfer component, the stabilizer, that is, one or more biocompatible non-ionic polymeric detergents according to this invention, can then be added to the IL-2 pool. Optionally, said mixture can be incubated before raising the pH of the now stabilized IL-2 pool to a pH of about 3.0 to 9.5, preferably 4 to 8.0, and more preferably 5 to 7.5. Incubation time depends mainly on the particular IL-2 analog, the particular composition of the stabilizer employed, the exact pH, and the concentrations of IL-2 protein and the stabilizer composition, but typically ranges from 0–100 minutes, preferably 10–100 minutes, more preferably 15–60 minutes, and most preferably 15–45 minutes.

Another method of avoiding strongly alkaline conditions during the diafiltration or desalting step, preferably desalting step, as the last step of purifying the recombinant IL-2 according to a process such as outlined in FIG. 1, is to perform said step without a transfer component but in the presence of a stabilizer of this invention at a pH range of from about 2 to about 5.5, preferably 3 to 4, and more preferably 3 to 3.5. The preferred buffer for such a diafiltration or desalting step, preferably desalting step, is an acetate buffer at a concentration of from about 5 to about 40 mM, preferably 10–30 mM, and more preferably 20 mM.

Said method comprises adding the stabilizer, for example, 0.1% Triton X305, prior to desalting or diafiltering, preferably desalting. When a fatty acid salt, such as sodium laurate, is employed as the primary solubilizing agent during the extraction and purification of the IL-2, the pH is adjusted to from about 2 to about 5.5, preferably 3 to 4, and more preferably 3 to 3.5, before the stabilizer is added. Upon pH adjustment to such a range, the fatty acid salt, preferably sodium laurate, precipitates from the pool, and is removed by centrifugation and filtration, or by other means known to those skilled in the art. An effective amount of the stabilizer is then added, optionally incubated, and diafiltered or desalted, preferably desalted, at a pH range of from about 2 to about 5.5, preferably 3 to 4, and more preferably 3 to 3.5. The formulation can then be maintained at such a pH range or the pH can then be adjusted to that desired for the formulation, that is, from about 3.0 to 9.5, preferably 4 to 8, and more preferably 5 to 7.5. As in the other lyophilization formulation routes of this invention, once the pH has been adjusted to that desired for the formulation, in immediate and continuous sequence, a bulking agent is added, the solution is optionally prefiltered and sterile filtered, and lyophilized. The formulation can then be reconstituted when needed for therapeutic administration.

When other than a fatty acid salt, for example, SDS, is employed as the primary solubilizing agent for extraction and purification of the recombinant IL-2, the above-described alternative method for diafiltration or desalting is performed in essentially the same manner, except it is not necessary to centrifuge and filter the IL-2 pool prior to desalting or diafiltration to remove a precipitate.

Alternatively, the diafiltration or desalting step, preferably desalting step, can be performed, in the absence of both a transfer component and a stabilizer, at a pH range of about 3 to about 3.5, preferably about pH 3.0. The preferred elution buffer is acetate at a concentration of from about 5 to 40 mM, preferably 10 to 30 mM, and more preferably 20 mM. When a fatty acid salt such as sodium laurate is the primary solubilizing agent during extraction and purification of the recombinant IL-2, it should be removed prior to diafiltration or desalting by lowering the pH of the IL-2 pool with an appropriate acidic agent, preferably HCl or acetic acid, to pH 3 to 3.5, preferably pH 3.0, at which point the fatty acid salt, preferably sodium laurate, precipitates and is removed by centrifugation and filtration or by other means known to those skilled in the art. The diafiltration or desalting step, preferably desalting step, is then performed at a pH range of 3 to 3.5, preferably at a pH of about 3. Then, the IL-2 pool is stabilized by adding a stabilizer according to this invention, optionally incubating the mixture, and then if a lyophilized formulation is desired, adjusting the pH to that desired for the formulation, and in immediate, continuous sequence, adding a bulking agent, optionally pre-filtering, sterile filtering, and lyophilizing the formulation.

When other than a fatty acid salt, for example, SDS, is used as the primary solubilizing agent for extracting and purifying the recombinant IL-2, the alternative procedure for desalting or diafiltration as described immediately above is essentially the same except that it is not necessary to centrifuge and filter the IL-2 pool prior to diafiltration or desalting, to remove a precipitate.

Although all of the above described processes for diafiltration or desalting immediately prior to formulation represent preferred methods for performing such a step, other procedures for diafiltration or desalting can be employed. For example, although it is preferable to avoid strongly alkaline conditions during diafiltration or desalting as indicated above, the IL-2 could be diafiltered or desalted at a pH range of from about 10.5 to 12.5, preferably at a pH of 11, to remove SDS or other strong detergent agents used during the extraction and purification of the IL-2. The desalted or diafiltered IL-2 pool can then be stabilized by the non-ionic biocompatible polymeric detergent stabilizers of this invention, before the continuous, immediate sequence of lowering the pH of the stabilized solution to a pH range of 3.0 to 9.5, preferably 4 to 8, more preferably 5 to 7.5, and adding a bulking agent, optionally pre-filtering, sterile filtering and lyophilizing.

A further aspect of this invention is to provide for extraction, purification and formulation processes wherein the formulated recombinant IL-2 is totally or substantially free of SDS or other strong detergent solubilizing agents. Said processes comprise the use of a non-toxic, milder detergent/chaotrope as the primary solubilizing agent instead of SDS or other strong detergent solubilizing agents during extraction, purification and recovery of the recombinant IL-2. Such non-toxic detergent/chaotropes include the fatty acid salts discussed above as transfer components, preferably laurate salts, and most preferably sodium laurate (0.5% to 3%, preferably 1.5–2.5%, and most preferably about 2%). The preferred pH range for solubilizing the refractile bodies of the E. coli expressed IL-2 with a fatty acid salt such as sodium laurate would be about 8.5 to about 10, preferably 9 to 9.5, and more preferably about pH 9.

When such fatty acid salts, such as sodium laurate, are used as the primary solubilizing agent, it is necessary, as exemplified in FIG. 2, to remove the fatty acid salt by centrifugation and filtration twice during the purification of the recombinant IL-2—once, prior to the preparative reverse phase high pressure liquid chromatography (RP-HPLC), and again (as indicated above in the description of alternative desalting or diafiltration steps) either prior to the diafiltration or desalting step, preferably the desalting step, or after lowering the pH to about 2 to 4 after diafiltering or desalting at pH 8.5 to 10.

Further, when a fatty acid salt, such as sodium laurate, is employed as the primary solubilizing agent, all column chromatography, for example, S200, G-25, RP-HPLC, is perforated at a pH range of from about 8.5 to 10, preferably 9 to 9.5, and more preferably 9 to 9.2, or is performed at a pH range of 2 to 5.5, preferably 3 to 4, and most preferably 3 to 3.5. Appropriate buffers for said pH ranges are employed.

A comparison of FIG. 1 illustrating a preferred embodiment wherein SDS is the primary solubilizing agent and FIG. 2A-B wherein sodium laurate is the primary solubilizing agent, further exemplifies the differences between such procedures.

Also, as described above and illustrated in FIG. 5, another primary solubilizing agent which can be used as an alternative to SDS or other strong solubilizing agents in the extraction and purification of recombinant IL-2 is guanidine hydrochloride (5–8M, preferably about 7M). It is preferred that when such alternative solubilizing agents are employed that the refractile bodies containing the recombinant IL-2 be at a concentration from about 5 to 10 mg/ml, preferably 7 to 8 mg/ml.

Further, the invention provides an improved formulation process which further avoids the creation of IL-2 aggregates in lyophilized formulations. Said process comprises performing the steps of adjusting the pH to the desired range of the formulation, bulking agent addition, pre- and sterile filtration and lyophilization in a continuous immediate sequence. Variants of such formulation steps can also be performed so long as lyophilization occurs shortly after neutralization.

Further, this invention provides for methods of screening from known biocompatible non-ionic polymeric detergents and combinations of said detergents to find stabilizer for the IL-2 formulations of this invention. In general, candidate non-ionic detergents or combinations thereof can be screened as stabilizers for IL-2 processed according to the preferred methods described above wherein the IL-2 is denatured and then renatured in the presence of a chaotrope, by adding them at appropriate concentrations to appropriate dosage amounts of the IL-2 and periodically testing for bioactivity, preferably by a cell proliferation assay (HT-2) according to Gillis et al., *J. Immunol.*, 120:2027–2032 (1978), and stability, for example, by visual inspection for clarity, over a test period, preferably from about 4 to about 24 hours at room temperature.

For IL-2 extracted and purified according to procedures other than the preferred procedures which comprise the steps of renaturing the IL-2 in the presence of a chaotrope, as, for example, IL-2 extracted and purified by a process according to FIG. 1, wherein SDS is the primary solubilizing agent used throughout the process, a preferred screening method comprises the steps of:

a. passing extracted, partially purified recombinant IL-2 in about 0.1% SDS through a desalting column equilibrated in 0.1% sodium laurate in a low ionic strength elution buffer at pH 8.5–9.5 to obtain an eluate of IL-2;

b. lowering the pH of the eluate with an appropriate acidic agent to about pH 2–3.3;

c. centrifuging and filtering the eluate to remove the precipitated sodium laurate;

d. adding to the desalted pool an appropriate concentration of the candidate biocompatible non-ionic polymeric detergent or of the candidate combination of said detergents;

e. adjusting the pH to 3.0 to 9.5 pH with an appropriate basic agent; and f. allowing the IL-2 pool to stand for 24 hours at a pH range of 3.0 to 9.5.

If said candidate stabilizer maintains the recombinant IL-2 in solution at pH 3.0 to 9.5 over a 24 hour period, it is considered for inclusion in the prototype formulations of this invention. Preferably, the concentration of the elution buffer in step (a) is 5 to 20 mM, preferably 10 mM. The elution buffer of step (a) is preferably 10 mM Tris-HCl at pH 9.0; 10 mM borate at pH 9.1 or 9.8; or 10 mM NaOH at pH 10.8.

Further preferred is a screening method wherein the pH range for steps (e) and (f) is about 4 to about 8. A still further preferred screening method is that wherein the pH range for steps (e) and (f) is about 5.0 to about 7.5.

To analyze prototype formulations, ultracentrifugation is used as a simple method of detecting the presence of high molecular weight aggregates and oligomers. Such candidate formulations can also be screened by SDS-PAGE under non-reducing conditions and by Western blot. Reverse phase chromatography can also be used to test for the presence of aggregates.

A preferred process for preparing the recombinant IL-2 formulations of this invention wherein the IL-2 is not denatured and renatured in the presence of a chaotrope comprises the steps of: (a) extracting the recombinant IL-2 from the disruptate of a host organism transformed to produce the IL-2 protein; (b) purifying the IL-2 protein using a desalting step at a pH range of 8.5 to 10 employing a fatty acid salt having from about 10 to about 13 carbons as a transfer component as the last step of purification; (c) lowering the pH of the desalted pool to about 2 to about 4; (d) centrifuging and filtering the IL-2 pool to remove the precipitated fatty acid salt; (e) mixing the purified IL-2 in an inert carrier medium with an effective amount of a non-ionic biocompatible polymeric detergent or a combination of non-ionic biocompatible polymeric detergents at a pH of about 2 to about 4; (f) incubating the mixture for from about 0 to 100 minutes; (g) adjusting the pH to a range of about 3.0 to about 9.5; (h) adding an effective amount of a polyol bulking agent; (i) optionally pre-filtering and sterile filtering the solution; and (j) lyophilizing the formulation.

Preferably the transfer component of step (b) is sodium laurate and said desalting step is performed at a pH of 9 to 9.5, most preferably 9 to 9.2, the pH range for step (c) is 3 to 4, more preferably about pH 3.5, and the pH range for step (g) is between 4 and 8, and more preferably from 5 to 7.5.

FIGS. 1 through 3 illustrate the details of the individual process steps of embodiments of the present invention including the culture of the transformed microorganisms in an appropriate fermentation medium through the final step where the purified IL-2 is stabilized and may then be lyophilized to be later reconstituted into therapeutic formulations for clinical administration.

The individual process steps of such an example of one embodiment of the instant invention wherein the primary solubilizing agent is SDS as in FIG. 1 are summarized as follows:

(a) growing the transformed bacterial hosts in an appropriate fermentation medium;
(b) concentrating the bacteria in the fermentation medium by cross-flow filtration, centrifugation or other conventional methods;
(c) disrupting the cell wall and cell membrane of the bacteria;
(d) removing greater than 99% by weight of the salts from said disruptate by diafiltration or centrifugation;
(e) redisrupting the desalted disruptate;
(f) adding a material to the disruptate to increase the density or viscosity of the liquid within the disruptate;
(g) separating the refractile material from the cellular debris by high-speed centrifugation;
(h) solubilizing the refractile material with SDS in an aqueous buffer;
(i) isolating said refractile material from the extractant by centrifugation;
(j) adjusting the pH of the solution to about 8.5 and reducing the solubilized IL-2 with dithiothreitol;
(k) lowering the pH to about 5.5 and purifying the reduced IL-2 by chromatography;
(l) collecting the eluted fraction of the purified IL-2 and oxidizing it at about pH 7 with $CuCl_2$ in a 1:3 mole-to-mole (protein to $CuCl_2$) ratio;
(m) concentrating the oxidized IL-2 at a pH of about 5.5, filtering it at a pH less than or equal to 3 and then subjecting it to preparative reverse phase high pressure liquid chromatography (RP-HPLC);
(n) precipitating the IL-2 by adding phosphate buffer to the HPLC pool;
(o) solubilizing the HPLC precipitate in a phosphate buffer;
(p) further purifying the IL-2 by gel chromatography and the eluate containing the purified IL-2;
(q) as the last step of purification, desalting the IL-2 on a desalting column employing an elution buffer of low ionic strength containing 0.1% sodium laurate as a transfer component at a pH of about 9-9.5;
(r) lowering the pH of the desalted pool to about pH 3 at which point the sodium laurate precipitates;
(s) centrifuging and filtering to remove the precipitated sodium laurate;
(t) formulating the IL-2 with an appropriate biocompatible non-ionic polymeric detergent at a concentration of from about 0.075% to about 3% by volume;
(u) optionally incubating the mixture at a pH range of about 3;
(v) neutralizing the mixture by raising the pH to about 7.0 to 7.8;
(w) adding an appropriate bulking agent in a concentration of from about 3.0% to about 7%;
(x) pre- and sterile filtering the solution;
(y) optionally lyophilizing the IL-2 formulation; and
(z) reconstituting the lyophilized IL-2 sample, when appropriate, for clinical administration.

The IL-2 is oxidized in step (1) preferably by the methods described in U.S. Pat. No. 4,572,798 to Koths et al. using copper chloride. The oxidation step is preferably carried out so that the IL-2's cysteine residues are bridged to form cystines. Alternatively, the IL-2 can be oxidized by the methods described in U.S. Pat. No. 4,530,787 to Shaked et al., using an o-iodosobenzoic acid solution. The disclosures of both of these patents are herein incorporated by reference.

Also, herein incorporated by reference is the disclosure of EP 206,828, which details the procedures for extracting and purifying recombinant proteins, such as IL-2, which are deposited within the microbial host in refractile bodies, focusing on the isolation of the refractile materials by front-end processes which are either "abbreviated" or "expanded".

The IL-2-producing transformed microorganisms are grown in a suitable growth medium, typically to an optical density (OD) of at least about 30 at 680 nm. The composition of the growth medium will depend upon the particular microorganism involved. The medium is an aqueous medium containing compounds that fulfill the nutritional requirements of the microorganism. In expression vectors involving the trp promoter, the tryptophan concentration in the medium is carefully controlled to become limiting at the time IL-2 expression is desired.

After the cells are harvested from the culture, they may be concentrated, if necessary, to about 20 to 150 mg/ml by cross-flow filtration, centrifugation, or other conventional methods. Preferably a compound which is non-toxic to humans, such as 1-octanol, in an amount of about 1% by weight of total components, is added to the fermenter before or during cell concentration to ensure that no viable recombinant organisms remain before containment is broken.

Following concentration of the harvested culture, the cell walls and membranes of the microorganisms are disrupted. Conventional cell disruption techniques such as homogenization, sonication, or pressure cycling may be used in this step of the process. After the cells have been disrupted, deionized water is preferably added to the disruptate and greater than 99% by weight of the salts are removed therefrom.

After the salts are essentially removed, optionally a compound such as 1-octanol may be added to the desalted disruptate, if not added earlier, to ensure that no viable recombinant organisms remain. The desalted disruptate is again disrupted as described above for the initial disruption. After redisruption, density or viscosity is increased in the liquid within the disruptate by adding a material to the disruptate.

In the final step of the abbreviated front-end process to recover the refractile bodies, the refractile bodies containing the desired protein are separated from the cellular debris by high-speed centrifugation. The pellet resulting from this centrifugation is called the "particle pellet" or "particle paste." The abbreviated front-end process is most preferably used when a fatty acid salt, such as sodium laurate, is the primary solubilizing agent.

A variety of different process alternatives as indicated above are available at this point. One preferred route illustrated in FIG. 5 is that employing a chaotropic agent to dissolve and denature the IL-2 in the particle paste or pellet by mixing the paste/pellet with a solution of a strongly denaturing concentration of the chaotropic agent and a reducing agent. The chaotropic agent and reducing agent are in an aqueous buffer at pH 7 to 9, preferably phosphate buffered saline. Adjustment of pH may be accomplished by the addition of base such as NaOH. The w/v ratio of pellet to solution will normally be in the range of 0.01:1 to 0.25:1, preferably 0.05:1 to 0.12:1 reducing agents that can be employed during the dissolving/denaturing step include: β-mercaptoethanol, glutathione, cysteine and dithiothreitol (DTT). DTT is the preferred reducing agent. The concentration of the reducing agent in the medium will usually range between about 10 to 100 mM, with approximately 50 mM being the preferred concentration. Chelating agents such as ethylene diaminetetraacetic acid (EDTA) in concentrations of 1 to 50 mM, preferably about 25 mM, and buffers such as Tris HCl at concentrations of 25 to 250 mM, preferably 50 mM, may be included in the solution. Elevated temperatures in the range of 35° C. to 50° C., preferably about 40° C., and a nitrogen blanket are used in this step. The dissolution/denaturation will typically be complete after about 5 to 15 min. of mixing. After this time, the mixture is centrifuged, preferably at 2000×g to 4000×g for about 10 to 30 min., to remove any undissolved materials.

The denatured IL-2 is next subjected to a controlled oxidation. The reducing agent is first removed by gel filtration or diafiltration. Gels that are capable of removing the reducing agent from the protein solution are commercially available. After removing the reducing agent the protein solution is diluted, if necessary, with the solution of chaotropic agent to a protein concentration of about 0.1 to 2 mg/ml, preferably about 0.25 to 0.5 mg/ml.

Preferred selected oxidation procedures as indicated above are used. The $Cu^{+2}$ oxidation comprises reacting the aqueous solution of denatured IL-2 at a pH between about 5.5 and 9, preferably 6 to 8, and most preferably about 7.5, in the presence of air with at least an effective amount of an oxidation promoter containing a $Cu^{+2}$ cation. The pH is maintained between 5.5 and 9, preferably between 7 and 8, in the -o-iodoso-benzoic acid oxidation.

The reduced IL-2 must remain in solution for effective oxidation to occur. Therefore, the reaction mixture must contain a sufficient concentration of chaotropic agent to keep the reduced IL-2 in solution. As indicated above, when guanidine hydrochloride is used, its concentration must be above 6 M. At such concentrations, a substantial amount of the IL-2 will be in a denatured form. For this reason, it is not possible in the case of IL-2 to carry out the oxidation and renaturation simultaneously and obtain high yields of renatured IL-2.

The temperature used in the oxidation will normally be between about 20° C. and 40° C., conveniently room temperature. For $Cu^{+2}$ oxidation, increasing the reaction temperature increases the rate of reaction. The oxidation reaction may be effectively terminated by, e.g., lowering the pH to a level at which the reaction ceases, freezing the solution, or adding chelators such as EDTA to the reaction mixture. Oxidation time will normally be in the range of 4 hr. to about one day.

When the oxidation is complete, the solution of oxidized, denatured IL-2 is diluted with buffer to reduce the concentration of chaotropic agent (guanidine hydrochloride) to a level that permits the oxidized IL-2 to renature and refold into the configuration of native IL-2. Phosphate buffer, 10 to 100 mM, preferably about 10 mM, is a preferred diluent. Preferably the IL-2 is concentrated using a hollow fiber membrane to avoid handling large volumes of solution. The concentration of guanidine hydrochloride agent is normally diluted to below about 2 M, preferably below about 0.5 M. The dilution will typically be carried out at about 4° C. to 25° C.. At such temperatures and reduced guanidine hydrochloride concentration a precipitate of extraneous host protein forms. This precipitate is removed by filtration or centrifuging to provide a supernatant containing the oxidized, renatured IL-2.

The renatured, oxidized IL-2 is then purified to remove endotoxins to a level that meets clinical specifications. The purification may be achieved by a combination of hydrophobic interaction and ion exchange chromatography or by RP-HPLC.

In the hydrophobic interaction/ion exchange chromatography technique, (NH$_4$)$_2$SO$_4$ is added to the IL-2 solution to a concentration of at least about 1.0 M, preferably about 1.25 M. The solution is then loaded onto a hydrophobic interaction column, such as a phenyl agarose column (e.g., Pharmacia Phenyl Fast-Flow Sepharose column). Bound IL-2 is recovered from the column with a decreasing (NH$_4$)$_2$SO$_4$ gradient, with the IL-2 being collected in the fractions eluting at about 0.75 M (NH$_4$)$_2$SO$_4$. Species of IL-2 and other impurities (bacterial host proteins) having lower isoelectric points than native IL-2 are then removed by cation exchange chromatography using an exchanger that binds IL-2 at a pH of 6 to 7.5. A carboxymethyl agarose column (e.g., Pharmacia Fast-Flow Sepharose CM) is a preferred preparative cation exchanger. The solution is contacted with the exchanger at the indicated pH range and the IL-2 is eluted from the exchanger using an ionic gradient. The desired IL-2 elutes at approximately 0.15 M salt with the lower isoelectric point forms of the protein eluting at lower salt concentrations.

The HPLC purification of the renatured IL-2 may be carried out in essentially the same manner as described in U.S. Pat. No. 4,569,790 followed by redissolution in the chaotropic agent and dialysis. Briefly, the solution of IL-2 is chromatographed and precipitated, and the resulting precipitate is taken up in the chaotropic agent solution. The chaotropic agent is then removed by dialysis or diafiltration. The IL-2 may be further purified by cation exchange chromatography.

The purified IL-2 is rendered aqueous, its concentration is adjusted, if necessary, to about 0.01 to about 2 mg/ml, and one or more non-ionic detergents of this invention are added thereto, and if the composition is to be lyophilized, one or more suitable bulking/stabilizing agents are then added, preferably those that provide an amorphous environment, and the composition is lyophilized shortly thereafter according to the methods indicated herein.

An alternative process illustrated in FIGS. 3 and 4 is that wherein the IL-2-containing particle pellet or paste is solubilized by mixing it with a neutral aqueous buffer containing a solubilizing agent and a reducing agent. Surfactants (detergents) which have a suitable hydrophobic-hydrophilic balance to solubilize the IL-2 may be used as solubilizing agents. Alkali metal sulfates containing 10 to 14 carbon atoms and alkali metal alkyl sarcosinates are preferred solubilizing agents, with SDS and sarcosyl being particularly preferred. Optionally, the aqueous buffer can also contain a chelating agent in a concentration of from 3 to 7 mM. EDTA at a concentration of 5 mM is a preferred chelating agent.

The amount of solubilizing agent used in the solubilization will depend upon the particular agent. When SDS or sarcosyl is used, the preferred concentration (w/v) of SDS/sarcosyl is 0.1%-10% in buffer such as PBS (50 mM sodium phosphate, pH 7, 0.9% sodium chloride). Preferably the range of SDS would be from 2% to 7%, most preferably 5%. The solubilizing medium also contains a sufficient amount of reducing agent to prevent the solubilized IL-2 from undergoing oxidation to any significant degree. Protein reducing agents such as DTT and 2-mercaptoethanol may be used for this purpose. The concentration of reducing agent such as DTT in the medium will usually range between about 5 and 30 mM, and is preferably about 20 mM. The solubilization will typically be carried out at temperatures in the range of 20° C. to 25° C. with mixing. Optionally, a reduction step may be carried out at this point. The pH, if necessary, may be adjusted to a range of 8 to 9, most preferably approximately 8.5. The suspension may be heated to 50±5° C. for 5 to 15 minutes under nitrogen. The reaction mixture is then cooled to approximately 25° C.

The solubilization is considered complete when the sample has sat 15 minutes or the solution turns translucent. Optionally at this point, the insoluble material may be separated by centrifugation or filtration after completing the solubilization.

The next step in the process is to remove the reducing agent from the solubilized IL-2 so that the solubilized IL-2 may be oxidized. Gel filtration is a preferred way of removing the reducing agent. The gel filtration will typically be run in buffered solutions (pH 5.5 to 7.0) containing about 0.1% to 1.0% solubilizing agent. The gel column will be sized to permit suitable resolution of the components.

Diafiltration may be used as an alternative to gel filtration to remove the reducing agent.

The IL-2 is next subjected to a controlled oxidation as described above. Following oxidation, the IL-2 is purified to remove endotoxins to a level that meets clinical specifications. RP-HPLC is a preferred method for effecting such purification. Supports (stationary phases) that provide good resolution of proteins may be used in the RP-HPLC purification. C-4, C-8, or C-18 on 300 angstrom pore-size supports are examples of preferred stationary phases. The separation is carried out at an acidic pH of less than about 2.3, usually 2.1 to 2.3. The solution of oxidized IL-2 is loaded onto the RP-HPLC column and is adsorbed onto the stationary phase. A gradient solvent system comprising an organic acid, such as acetic acid or trifluoroacetic acid, and organic solvent, such as 2-propanol or acetonitrile, is used to elute the IL-2 from the column. Acetic acid-propanol, trifluoroacetic acid-propanol, and trifluoroacetic acid-acetonitrile are preferred solvent systems. The elution conditions are similar to those described in U.S. Pat. No. 4,569,790, the disclosure of which in this regard is incorporated herein by reference.

The RP-HPLC pool may be used directly in the renaturation step, or the IL-2 may first be recovered as a "paste" from the pool by adding a neutral aqueous buffer, such as phosphate buffered saline (PBS), to the pool, allowing precipitation to occur, and recovering the solids by centrifugation.

The pool or paste is combined with an aqueous solution of a chaotropic agent present at a concentration that causes the IL-2 to be denatured. The chaotropic agent is preferably in an aqueous buffer, preferably PBS, at pH about 5 to 9, preferably about 7. Adjustment of pH, if necessary, may be accomplished by the addition of base such as NaOH. The amount of pellet/paste in the chaotropic agent solution will normally be in the range of 0.1 to 100 mg/ml, preferably 0.5 to 60 mg/ml. The denaturation step is typically carried out at temperatures in the range of about 4° C. to about 25° C., preferably 4° C. to 10° C., with mixing. The denaturation will typically be complete after about 5 to about 15 min. of mixing. A solid, which is believed to be mainly residual solubilizing agent (SDS), is formed during the denaturation. This solid is removed from the solution by filtration or other conventional solid-liquid separation techniques. The IL-2 is then renatured from the filtered chaotropic agent solution by reducing the concentration of chaotropic agent and protein concentration in the solution by diluting the solution with a neutral aqueous buffer or by dialysis or diafiltration against a neutral aqueous buffer. The protein concentration during renaturation will normally be in the range of 0.1 to 2.5 mg/ml, preferably 0.5 to 1.5 mg/ml.

If an IL-2 which does not have the cysteine residue at position 125 replaced with a neutral amino acid (such as IL-2 having the amino acid sequence of native IL-2) is being renatured, it has been observed that a significant amount of IL-2 isomers having different disulfide bridging than native IL-2 is formed. For this reason, it is preferred to carry out this process on IL-2s in which the cysteine residue at 125 is so replaced.

Following the renaturation, the renatured IL-2 may be further purified by ion exchange chromatography to remove forms of the protein which have lower isoelectric points than native IL-2 and other impurities. Cation exchangers may be used for this purpose which bind IL-2 at a pH of about 6 to 7.5. Carboxymethyl agarose columns (e.g., Pharmacia Fast Flow CM Sepharose) are preferred preparative cation exchangers. The solution of renatured IL-2 is contacted with the exchanger at the indicated pH range and the IL-2 is eluted from the exchanger using an ionic gradient. The desired IL-2 elutes at approximately 0.1 M salt with the lower isoelectric point forms of the protein eluting at lower salt concentrations.

The renatured, oxidized purified IL-2 can then be formulated in accordance with this invention.

Another alternative process for extracting and purifying the IL-2 is an expanded front-end process to recover the refractile bodies, wherein the particle pellet obtained from the last centrifugation step of the abbreviated front-end process is solubilized, reduced and then extracted from the aqueous medium with 2-butanol or 2-methyl-2-butanol. The extractant phase is then precipitated with an acid and centrifuged to produce a "final pellet" or "final paste" which is then further purified as indicated.

The additional steps of the expanded front-end process result in enhanced purity of the final pellet as opposed to the particle pellet, which lessens the purifying burden of downstream processing. Once the choice of the particular front-end recovery of the refractile bodies has been made, one skilled in the art can pick and choose the alternative purifying steps outlined below to achieve the desired purity level of the final product.

For solubilizing the refractile bodies containing the recombinant IL-2, the following solubilizing agents can be used: sodium dodecyl sulfate (SDS), sodium laurate, urea, sodium dodecyl sulfonate, sodium decyl sulfate, sodium tetradecyl sulfate, sodium tridecyl sulfonate, sodium dioctylsuccinate, sodium dodecyl N-sarcosinate, guanidine hydrochloride and sodium tetradecyl N-sarcosinate. Preferred solubilizing agents are SDS, guanidine hydrochloride and sodium laurate. Sodium laurate and guanidine hydrochloride are particularly preferred when it is desired to have a final container product substantially or totally free of SDS or other strong detergents.

The solubilizing agent is in an aqueous buffer, preferably phosphate buffered saline. The preferred percentage of the solubilizing agent is in the range of 1% to 5% (w/v). (Percentages herein reflect weight to volume ratios.) The particularly preferred concentration ranges and conditions for sodium laurate and guanidine hydrochloride as primary solubilizing agents are noted above.

Reducing agents that can be employed during the solubilization step include: mercaptoethanol, glutathione, cysteine and dithiothreitol (DTT). DTT is the most preferred reducing agent.

The refractile material containing the IL-2 bodies is preferably solubilized by contact with a neutral aqueous buffer containing not only a solubilizing agent but also a reducing agent. Surface active agents (detergents) which have a suitable hydrophobichydrophilic balance to solubilize the hydrophobic IL-2 protein may be used as solubilizing agents. Optionally, said aqueous buffer can also contain a chelating agent in a concentration of from 3 to 7 mM. Most preferably, said chelating agent is EDTA at a concentration of 5 mM.

The solubilization will typically be carried out at temperatures in the range of 20° C. to 25° C. with mixing to facilitate contact between the solid phase and the solubilizing medium. Optionally, a reduction step may be carried out at this point. The pH, if necessary, may be adjusted to a range of 8 to 9, most preferably approximately 8.5. The suspension may be heated to 50±5° C. for 5 to 25 minutes under nitrogen. The reaction mixture would then be cooled to approximately 25° C.

The solubilization is considered complete when the sample has sat 15 minutes or the solution turns translucent. Optionally at this point, the insoluble material may be separated by centrifugation or filtration after completing the solubilization.

If a reduction step was not carried out during the solubilization, the next step in the process is a reduction of the solubilized refractile body protein. A preferred reducing agent is dithiothreitol (DTT). Reduction conditions may also include the addition of a chelating agent such as ethylenediaminetetraacetic acid (EDTA).

The next step in the process is to separate the protein in the supernatant from any host contaminants remaining after the centrifugation or filtration and optimally from the solubilizing agent. Gel filtration chromatography, reverse-phase high performance liquid chromatography (RP-HPLC), or a combination of gel filtration chromatography and RP-HPLC, can be used. The gel filtration chromatography is preferably carried out in two stages that remove both pyrogenic components and protein contaminants having molecular weights higher or lower than that of the protein. Gels that are capable of fractionating the solution to permit separation of the protein from these contaminants are commercially available. Sephacryl ® S-200 is a preferred gel for removing the higher molecular weight components and Sephadex ® G-25, G-75 or G-100 gels are preferred for removing the low molecular weight contaminants. The gel filtrations will typically be run in buffered solutions (pH 7.0 to 9.2) containing about 0.1% to 1.5% solubilizing agent and about 0.5 to 10 mM reducing agent. The column will be sized to permit suitable resolution of the desired components.

RP-HPLC is an alternative to gel filtration. Also, RP-HPLC is capable of removing molecules from the solution that have molecular weights close to the protein and cannot, therefore, be removed completely by gel filtration. In addition, contaminants such as bacterial endotoxin are also removed effectively by RP-HPLC. Therefore, RP-HPLC may also be used as a final purification step after gel filtration.

An alternative and preferred procedure is to oxidize selectively, under controlled conditions, the IL-2 protein after it has been separated by gel filtration, as described above. The oxidized product is purified by RP-HPLC or gel filtration followed by RP-HPLC.

It is preferred in carrying out such an alternative process of this invention that the last step of purification before stabilization of the formulation is a desalting step optionally employing a transfer component, such as sodium laurate.

The purity of the protein after the chromatography step(s) is at least about 95% and usually at least about 98%. This highly pure material contains less than about 5 ng endotoxin, usually less than about 0.01 ng endotoxin per 100,000 units protein bioactivity.

The preferred processes of this invention for extracting, purifying and formulating IL-2 result in a substantially homogeneous final product wherein the IL-2 has the same disulfide bridging as native IL-2 and is substantially free of oligomers, containing less than about 15% by weight of isomers, and preferably less than 1% by weight isomers, having disulfide bridging different from native IL-2.

Although the above-referenced methods are the most efficient and effective procedures known to the inventors for extracting and purifying recombinant IL-2, recombinant IL-2 extracted and partially or completely purified by any methods known by those skilled in the art, can be stabilized and formulated with biocompatible non-ionic, polymeric detergents screened according to the procedures of this invention. For example, processes for extraction and purification, such as those described in references cited in the Background section herein, can be used to recover and purify the recombinant IL-2 for formulation according to this invention with non-ionic biocompatible polymeric detergents.

The formulation of the protein in accordance with this invention may be carried out as a separate operation using purified, selectively oxidized protein or in an operation that is integrated with the purification of the selectively oxidized protein. In the latter case, the starting material for the formulation is a proteincontaining product from a RP-HPLC treatment of the selectively oxidized product. Preferably a product selectively oxidized by the RP-HPLC product (pool) will comprise a solution of the protein in a water-organic solvent mixture. The nature of the organic solvent will depend upon the solvent system used in RP-HPLC.

Optionally, the first step in one formulation of the IL-2 protein from such an RP-HPLC pool is to render the mixture aqueous by resuspending (diluting) the pool in an aqueous buffer containing a solubilizing agent, such as sodium laurate, guanidine hydrochloride, SDS or sarcosyl, which enhances the solubility of the protein in water. Following this dilution the organic phase is removed from the protein-containing aqueous phase and the detergent concentration is reduced by diafiltration or desalting using an appropriate buffer and optionally a transfer component. Following diafiltration or desalting, the IL-2 protein concentration is readjusted to a concentration in the range of about 0.01 to 10 mg/ml, preferably 0.25 to 1.0 mg/ml.

The bulking agent adds bulk to the formulation such that when unit dosage amounts of the solution are lyophilized in containers, such as sterile vials, the freeze-dried residue will be clearly discernible to the naked eye.

The unit dosage amounts of the recombinant IL-2 protein are dispensed into containers, the containers are capped with a slotted stopper, and the contents are lyophilized using conventional freeze-drying conditions and apparatus.

The lyophilized mixture may be reconstituted by injecting a conventional parenteral aqueous injection such as distilled water for injection, Ringer's solution injection, 5% Normal Serum Albumin (NSA), 5% Human Serum albumin (HSA), Hank's solution injection, dextrose injection, dextrose and salt injection, physiological saline injection, or the like, into the vial. The injection should be added against the side of the vial to avoid excess foaming. The amount of injection added to the vial will typically be in the range of 1 to 5 ml, preferably 1 to 2 ml.

The reconstituted formulation prepared as described above is suitable for parenteral and oral administration to humans or other mammals in therapeutically effective amounts (i.e., amounts which eliminate or reduce the patient's pathological condition) to provide therapy thereto. IL-2 therapy is appropriate for a variety of immunomodulatory indications such as T cell mutagenesis, induction of cytotoxic T cells, augmentation of natural killer cell activity, induction of IFN-gamma, restoration and enhancement of cellular immunity (e.g., treatment of immune deficient conditions), and augmentation of cell-mediated anti-tumor activity.

The formulations of this invention are useful for parenteral administration, for example, intravenous, intraperitoneal, subcutaneous, intramuscular, intrathecal, intraorbital, opthalmic, intracapsular, intraspinal, intrasternal, topical, intranasal aerosol, scarification, and also, for oral administration. The preferred routes of administration are by intramuscular, subcutaneous and intravenous injection, and by topical administration. The use of non-ionic detergents is especially preferred for topically administered formulations because of their ability to penetrate the skin surface.

The following examples further illustrate the formulations and processes of the invention. These examples are not intended to limit the invention in any manner. In these examples all temperatures are in degrees Celsius unless otherwise indicated.

Example 1

This example illustrates a preferred process for recovering, purifying and formulating recombinant IL-2 wherein the IL-2 is not denatured and then renatured in the presence of a chaotrope.

An analog IL-2 designated des-ala$_1$-IL-2$_{ser125}$ was recovered from E. coli. The amino acid sequence of this recombinant IL-2 differs from that of native human IL-2 by the absence of the initial N-terminal alanine residue and by the substitution of a serine for a cysteine at position 125. The strain of des-ala$_1$-IL-2$_{ser125}$-producing E. coli (K12/MM294-1) carrying plasmid pLW45 used in this example was deposited at the American Type Culture Collection on Mar. 4, 1984 under accession number 39,626. Said analog is disclosed in U.S. Pat. No. 4,530,787 to Shaked et al. and prepared by the methods disclosed in U.S. Pat. Nos. 4,518,584 and 4,588,585 assigned to Cetus Corporation.

The E. coli thus transformed with plasmid pLW45 were grown in a 1000-liter fermentor at 37° C. The dissolved oxygen was maintained at about 40% by, as necessary; (1) increasing agitation; (2) adding air., and (3) adding oxygen.

Once the fermenter was filled with water to the operating volume, the following trace elements were added:

| | |
|---|---|
| ZnSO$_4$ · 7H$_2$O | 30 μM |
| MnSO$_4$ · 4H$_2$O | 30 μM |
| CuSO$_4$ · 5H$_2$O | 3 μM |
| Na$_3$ citrate · 2H$_2$O | 1.5 mM |
| KH$_2$PO$_4$ | 21 mM |
| (NH$_4$)$_2$SO$_4$ | 72 mM |

The fermenter feed and addition vessels were then sterilized according to standard operating procedures. Then the following sterile additions were made:

| | |
|---|---|
| MgSO$_4$ · 7H$_2$O | 3 mM |
| FeSO$_4$ · 7H$_2$O | 72 μM |
| L-tryptophan | 70 mg/L |
| thiamine · HCl | 20 mg/L |
| glucose | 5 g/L |
| tetracycline | 5 mg/L |

The fermenter was cooled and inoculated with frozen or seed E. coli culture at 2 mg/L. A glucose feed was employed to maintain the glucose concentration between 5–10 g/L. At approximately 15 hours after fermentation was begun, the pH was adjusted with KOH to 6.8. Optical density measurements and residual glucose measurements on samples were taken at 14–16 hours and approximately one hour intervals thereafter.

Induction of des-ala$_1$-IL-2$_{ser125}$ production by depletion of L-tryptophan from the culture medium occurred at about OD$_{680}$=10 followed by the addition of casamino acids to a final concentration of 2% at OD$_{680}$=15. Cultures were harvested about 3–5 hours later.

The refractile bodies containing the des-ala$_1$-IL-2$_{ser125}$ protein were then isolated. The harvested material is concentrated about 5–10 fold by circulating the harvest material under pressure through UF cross-flow filtration cartridges with a 100K molecular weight cutoff. The cells were washed with deionized water. EDTA was added to 25 mM, and the cells were disrupted by 3 passes through a disruptor at about 6500 psi.

After the suspension was diafiltered against 5 volumes of deionized water, EDTA was added to a final concentration of 5 mM. Octanol was added to 1% (v/v) to kill any residual live bacteria in the diafiltered product. After several hours, the diafiltered disruptate was redisrupted by passing it through a disruptor.

Sucrose was added to the redisruptate to create a final density between 1.1 and 1.25 9/ml. The mixture was centrifuged at 10,000 to 20,000×g at 1–2 1 pm, and the particle pellet or paste was collected. A temperature of at least 20° C. was maintained prior to and during centrifugation.

The particle paste was then solubilized in phosphate buffered saline with 5% SDS. The solubilized paste was then centrifuged at 25,000–35,000×g.

Solid DTT and EDTA were added to a final concentration of 50 mM and 2 mM, respectively. The suspension was heated to 50±5° C. for 20 minutes under nitrogen at a pH of about 8.5. The reaction mixture was then cooled to approximately 25° C., and then the pH of the mixture was readjusted to 5.5±0.1 using glacial acetic acid.

Chromatographic separation of the higher molecular weight contaminants was achieved using a Sephacry ® S-200 column. The solubilized and reduced refractile body protein was loaded onto the column and fractions were collected into clean, depyrogenated vessels using an elution buffer containing 50 mM acetate pH 5.5, 1 mM EDTA and 0.1% SDS. Peak fractions (those falling within 70% of the maximum peak height) were pooled and subjected to a controlled oxidation as follows:

The S200 pool was oxygenated by bubbling air through the solution, and the oxidation was initiated by adding CuCl$_2$ in a molar ratio of 1:3 (CuCl$_2$ to IL-2 protein). The oxidation was carried out at about 25° C. in 50 mM phosphate buffered saline. The pH was controlled at 7.0±0.2 during oxidation and adjusted to 5.5±0.2 when the oxidation was completed. Since oxidized IL-2 was more hydrophilic than reduced IL-2, the progress of the oxidation reaction was monitored by RP-HPLC.

The oxidized IL-2 was then concentrated using a hollow fiber ultrafiltration unit with a 10,000 molecular weight cutoff. The pH of the oxidized pool was then adjusted to pH of about 2 to about 3 and filtered through a 0.45 μM nitrocellulose filter.

Preparative HPLC using a Vydac ® C$_4$ bonded phase silica gel column supplied with two solvents was the next step in the IL-2 purification scheme. Solvent 1 was 6% acetic acid and 10% 2-propanol, and solvent 2 was 6% acetic acid and 94% 2-propanol. After pumping solvent 1 for 30 minutes, the acidified IL-2 protein was loaded. The column was developed with a gradient of solvents 1 and 2 and the protein which eluted at about 40% solvent 2 was pooled into a depyrogenated graduated cylinder.

In a 1:1 (volume to volume) ratio, 0.8 N NaOH was then added to the pooled protein, causing the protein to precipitate. The precipitated protein was then solubilized in 0.1 M Na$_2$HPO$_4$ with 1% SDS.

The final chromatographic step in the purification of IL-2 involved a second Sephacryl ® S-200 column. The primary objective of this column was to separate the IL-2 monomer fractions from higher molecular weight oligomers of the protein. The column was eluted with buffer containing 50 mM acetate pH 5.5, 1 mM EDTA and 0.1% SDS, and IL-2 monomer fractions were pooled.

A desalting G-25 column was then equilibrated with 0.1% sodium laurate in 10 mM Tris-HCl and loaded with the IL-2 monomer fractions collected from the S-200 column. The G-25 column was run at pH 9.1. Using a process chromatogram, the des-ala$_1$-IL-2$_{ser125}$ peak was collected. The pH of the eluate was then lowered quickly with 1.0 N HCl to pH 3.0, which precipitated the sodium laurate, but left the des-ala$_1$-IL-2$_{ser125}$ in solution.

The IL-2 recovery from the S-200 pool was 76.7%. SDS concentration was assayed by acridine orange. [Sokoloff et al., "Rapid Spectrophotometric Assay of Dodecyl Sulfate Using Acridine Orange," Anal. Biochem., 118:138–141 (1981).] The SDS concentration was less than 10 μg/mg, more specifically, 3.8 μg/mg.

The samples were centrifuged and filtered to remove the precipitated sodium laurate. Then at pH 3.0 Triton X305 and Triton X405 were respectively added at 0.1% to 1 ml samples of the IL-2 pool. Then the PH of each sample was raised to 7.5. Then in immediate continuous sequence, 5% mannitol was added to each sample, the samples were pre-filtered and sterile filtered, and the correct dosage amounts of the des-ala$_1$-IL-2$_{ser125}$ were aseptically filled into sterilized vials with sterilized stoppers under sanitary and sterile conditions that were carefully monitored. The vials were then quickly placed in a lyophilizer where appropriate thermocouples were attached.

The vials were frozen to between −35° and −45° C. The lyophilization cycle was completed, and the vials were mechanically sealed under a vacuum.

Example 2

This example illustrates a recovery, purification and formulation process which corresponds to that outlined in FIG. 2. The procedure essentially follows that of Example 1 for the recovery and purification of the recombinant IL-2 up to the desalting step with the differences noted below. As the procedures in this example were not performed, it is expressed in the present case.

In the paste solubilization step, 2% sodium laurate rather than 5% SDS is employed at pH 9.0. The reduction step is carried out at pH 9.2 with 1–2% sodium laurate rather than 5% SDS. The buffer for the first S200 column is 20 mM Tris.HCl and is carried out at pH 9.2 wherein 1–2% sodium laurate rather than 0.1% SDS is employed. Also the oxidation step and solubilization steps are carried out at pH 9.2 in 20 mM.Tris HCl; and for the solubilization step 1–2% sodium laurate is employed instead of 1% SDS. There is a centrifugation and filtration step just prior to RP-HPLC to remove precipitated sodium laurate. The second S200 column is also run in 20 mM Tris.HCl at pH 9.2 wherein 0.1–0.5% sodium laurate rather than 0.1% SDS is used.

Instead of running the G-25 column at pH 9–9.2 as in Example 1, the pH of the IL-2 pool is then adjusted to pH 3. The sodium laurate precipitates and is removed by centrifugation and filtration. The IL-2 pool is then stabilized with 0.1% Triton X305 and incubated for 15 minutes. Then the desalting step is performed on the G-25 column employing 20 mM acetate.

Then in immediate and continuous sequence the pH is raised to 7.0 with NaOH; 5% mannitol is added; and the solution is pre-filtered and then sterile filtered through a 0.45 μM nitrocellulose filter and 0.22 μM filter, respectively., and then lyophilized.

The primary advantage of the procedures of this example is to arrive at a formulation that is completely free of SDS.

Example 3

This example illustrates a method of screening for non-ionic biocompatible polymeric detergents or combinations of such non-ionic biocompatible polymeric detergents as stabilizers for the pharmaceutical compositions of this invention.

Des-ala$_1$-IL-2$_{ser125}$ solutions were prepared essentially according to the procedures of Example 1, up to but not including the step of bulking/stabilizing agent addition. Thus, the IL-2 pool was desalted in a G-25 column equilibrated with 0.1% sodium laurate in 10 mM Tris.HCl at pH 9 to 9.2. The des-ala$_1$-IL-2$_{ser125}$ peak was collected. The pH of the eluate was then lowered quickly with 1.0 N HCl to pH 3.0, at which point the sodium laurate transfer component precipitated. The samples were centrifuged and filtered to remove the precipitate, and then an appropriate amount of the candidate non-ionic biocompatible polymeric detergent as indicated in Table 1 was added to the samples.

The pH of the samples were then raised to that indicated in Table 1 for each representative stabilized solution and allowed to stand overnight. Solubility of the stabilized solutions was then checked the next day visually and by UV scan. Table 1 indicates the results of such solubility testing for representative stabilized solutions. No precipitation was observed by eye or by UV scan for any of the representative stabilized solutions listed in Table 1.

TABLE I

| | | |
|---|---|---|
| Triton X405<br>1 mg/ml of IL-2<br>Remains soluble at<br>pH 7.0 overnight<br>at room temperature | 0.1% | (v/v) |
| Triton X305<br>1 mg/ml of IL-2<br>Remains soluble at<br>pH 7.0 overnight<br>at room temperature | 0.1% | (v/v) |
| PEG (4000) Monostearate<br>1 mg/ml IL-2<br>Remains soluble at pH 7.0<br>for 24 hours at room<br>temperature | 0.1% | (wt/v) |
| PEG (4000) Monostearate<br>0.2 mg/ml IL-2<br>Remains soluble by UV scan<br>at pHs 6 and 7 for 24 hours<br>at room temperature | 0.05% | (wt/v) |
| PEG (4000) Monostearate<br>0.42 mg/ml IL-2<br>Remains soluble at pHs 6<br>and 7 for 24 hours at<br>room temperature | 0.01% | (wt/v) |

EXAMPLE 4

The procedures of Example 4 were repeated with each of the following concentrations (weight/volume) of PEG (4000) monostearate:
0.01%
0.05%
0.1%
0.5% and
1.0%.

The procedures were then repeated with each of the concentrations of PEG(4000) monostearate, except that the pH was raised to 5 and 6 respectively, instead of 7. At pH 5, 6 and 7, UV scan results indicated that the solubility at all such concentrations with PEG (4000) monostearate was acceptable, that is, the IL-2 protein stayed in solution after 24 hours.

The procedures outlined above in this example were repeated wherein the IL-2 from the second S-200 column was at a concentration of 0.2 mg/ml. The IL-2 remained soluble at pHs 5, 6 and 7, and at all concentrations of the PEG (4000) monostearate listed above.

EXAMPLE 5

Ultracentrifugation Data

Ultracentrifugation is a simple method of detecting the presence of high molecular weight aggregates and oligomers. Ultracentrifugation was performed in a Beckman L8-70 using a type 70.1 Ti rotor. Five milliliter samples of the stabilized solutions listed above in Table 1 were spun at 55,000 rpm for one hour. The supernatant was measured by absorbance at 280 nm. Said absorbance was then compared to that prior to centrifugation. Table 2 below shows the results of such testing.

TABLE 2

| Samples | Ultracentrifugation 55,000 rpm—60 min. % Recovery |
|---|---|
| 0.1% Triton X405 pH 7.0 0.25 mg/ml IL-2 | 95% |
| 0.1% Triton X305 pH 7.0 0.25 mg/ml IL-2 | 91% |
| 0.05% PEG (4000) monostearate 0.2 mg/ml IL-2 pH 6 and pH 7 | 100% |
| 0.01% PEG (4000) monostearate 0.4 mg/ml IL-2 pH 6 | 86.9% |
| 0.01% PEG (4000) monostearate 0.4 mg/ml IL-2 pH 7.0 | 91.1% |

The results in Table 2 indicate that all the representative stabilized IL-2 solutions contain very low levels or no aggregates or oligomers. Acridine orange assays for SDS in the PEG (4000) monostearate compositions at concentrations of 0.05% (0.2 mg/ml IL-2) and 0.01% (0.4 mg/ml IL-2) showed less than 1 μg/mg of SDS.

Example 6

Bioassay

Representative stabilized solutions of this invention as listed in Table 1 above were tested by bioassay as described in Gillis et al., *J. Immunol.*, 120:2027–2032 (1978). The results are indicated in Table 3 below.

TABLE 3

| Composition | Bioassay Results IL-2 Concentration | Units/mg |
|---|---|---|
| Triton X405 (0.1% pH 7) | 0.25 mg/ml | $2.44 \times 10^5$ |
| Triton X305 (0.1% pH 7) | 0.25 mg/ml | $1.17 \times 10^6$ |
| PEG (4000) monostearate (0.1% pH 7) | 0.4 mg/ml | $\geq 1.80 \times 10^7$ |

Example 7

Representative stabilized solutions as listed in Table 1 above were tested by reverse-phase high pressure liquid chromatography (RP-HPLC), sodium dodecyl sulfate polyacrylamide gel electrophoresis (SDS-PAGE), and Western blot with an anti-des-ala$_1$-IL-2$_{ser125}$ monoclonal antibody.

The Western blots indicated that the solutions stabilized with Triton X305 and Triton X405 (0.1% with 0.25 mg/ml IL-2) were roughly equivalent to compositions of IL-2 with 0.1% laurate (0.25 mg/ml IL-2) and 0.1% SDS (0.25 mg/ml IL-2).

Example 8

For each of the following representative stabilized IL-2 solutions listed in Table 3 below, 5 ml of the eluate from the second S-200 column in the IL-2 purification process as described in Example 1, containing 1.32 mg/ml of IL-2, was loaded onto a Sephadex G-25 column equilibrated in the buffer specified. No transfer component was used in the elution buffer. Between the running of each 5 ml IL-2 sample, the G-25 column was washed with 50 ml 0.1 N NaOH.

All samples were assayed by acridine orange. [Sokoloff et pid Spectrophotometric Assay of Dodecyl Sulfate Using Acridine Orange," *Anal. Biochem.*, 118:138–141 (1981).] No SDS was detectable in any of the representative formulations.

The results of such experiments are recorded below in Table 3. Any inaccuracies in the recovery data can be attributed to buffer absorbance.

TABLE 3

| Solubilizer/Stabilizer | Buffer pH | 20 mM for each | Recovery of IL-2 |
|---|---|---|---|
| 0.1% Triton X305 | 7.0 | phosphate | 110% (0.54 mg/ml) |
| 0.1% Triton X305 | 9.0 | Tris · HCl | 56% (0.18 mg/ml) |
| 0.1% MaPEG | 5.0 | citrate | 102% (0.28 mg/ml) |
| 0.1% Triton X305 | 5.0 | citrate | 100% (0.24 mg/ml) |
| 0.1% Triton X305 | 3.0 | citrate | 118% (0.26 mg/ml) |

This example indicates that SDS can be effectively removed by desalting the S-200 IL-2 pool over a wide pH range. The results further indicate that the representative biocompatible nonionic polymeric detergents can solubilize IL-2 over a wide pH range.

Example 9

This example illustrates another preferred process (outlined in FIG. 3) for recovering, purifying and formulating recombinant IL-2, wherein the IL-2 is denatured and renatured with guanidine hydrochloride.

The process of this example follows the procedure of Example 1 above (outlined in FIG. 1) through the preparative RP-HPLC step. Then, phosphate buffer was added to the HPLC pool to neutralize the pH, resulting in the formation of a precipitate ("HPLC paste"), which was recovered by centrifugation as a pellet.

Approximately one gram of the HPLC paste was washed and repelleted two times with 100 ml of 0.1 M citrate buffer (pH 6.5). The pellet was then dissolved in 100 ml of 7 M guanidine (10 mM citrate buffer. Fine particles were removed by filtering through a 0.2 micron filter. An additional 600 ml of guanidine buffer was added to the filtered solution, which was then diafiltered with a 1 square foot YM-10 spiral cartridge (Amicon). Cold citrate buffer (10 mM, pH 6.5) with 2.5% sucrose was used as the exchange buffer. The diafiltration rate was approximately two volume changes per hour. After six volume changes a cloudy solution was obtained which was then filtered through a 0.2 micron Nalgene flat filter with a prefilter insert. A yield of approximately 80% (800 ml, 1.12 mg/ml) was obtained.

Preparative ion exchange chromatography was performed on the diafiltered HPLC solubilized paste on a Pharmacia ® Fast Flow CM Sepharose column. Buffers used for gradient elution were pH 6.5 citrate buffer and citrate buffer with NaCl (0.04 to 0.5 M).

The ion exchange pool was then desalted on a G-25 Sephadex ® column into 10 mM citrate buffer at pH 6.5. The desalted IL-2 pool was then stabilized by the addition of 0.2% Tween ® 80 (volume/volume concentration) and 1% sucrose (weight/weight concentration). The pool was then sterile filtered through a 0.2 μm cellulose acetate filter. Immediately thereafter the correct dosage amounts of the IL-2 (des-ala$_1$-IL-2$_{ser125}$ at 1.0 mg/ml) were aseptically filled into sterilized vials with sterilized stoppers under sanitary and sterile conditions, which were carefully monitored. The vials were then quickly placed in a lyophilizer where thermocouples were attached. The vials were frozen to between −35° and −45° C. The lyophilization cycle was completed, and the vials were mechanically sealed under a vacuum.

Example 10

The formulations containing 1 mg/ml IL-2 listed in Table 4 below were prepared essentially according to Example 9 and tested by ultracentrifugation as outlined in Example 5. Unformulated IL-2 extracted and purified according to Example 9 serves as a control. The results shown in the Table 4 indicate that all the representative stabilized IL-2 solutions contain very low levels or no aggregates, dimers or oligomers.

TABLE 4

| Ultracentrifugation Data | |
|---|---|
| Formulation | % Recovered |
| Unformulated IL-2 | 93% ± 1.5% |
| 0.05% Tween ® 80<br>2% sucrose | 88% |
| 0.2% Tween ® 80<br>1% sucrose | 87% ± 3% |
| 0.1% MaPEG<br>1% sucrose | 87% ± 6% |

Example 11

A light scattering turbidity assay was used to measure the turbidity of sample formulations of this invention by using a fluorometer to measure the amount of light (510 nm) scattered from a sample formulation at 90° C. Representative lyophilized formulations listed in Table 5 were held at 4° C., reconstituted with distilled water and measured by the light scattering turbidity assay immediately and four hours after reconstitution (at room temperature). Indicated in Table 5 for each formulation are the pH, the selected non-ionic detergents and their concentrations (in v/v terms except for MaPEG which is expressed in wt/vol terms), and the selected bulking/stabilizing agents and their concentrations (wt/vol). The formulations were prepared just as outlined in Example 9, except that the desired concentrations of the selected nonionic detergents are substituted for the 0.2% Tween ® 80, and for those formulations indicated to be at pH 3.5, the non-ionic detergent and bulking/stabilizing agent were added in 10 mM citric acid at pH 3.5, thereby resulting in formulations at pH 3.5. The results listed in Table 5 are an average of 6 vials of each representative formulation containing 1 mg/ml of IL-2.

The assay is premised on turbidity being indicative of the presence of precipitates, particulates, aggregates and oligomers. The turbidity is measured in units wherein formulations registering below 1000 units are clear to the eye and wherein a difference of plus or minus 25 units is not considered statistically significant. The results indicate that all of the representative lyophilized formulations are clear to the eye and that none increase significantly in turbidity upon standing at room temperature after reconstitution.

TABLE 5

| Light Scattering Turbidity Assay | | |
|---|---|---|
| Formulation | Initial Scattering | Scatter After 4 Hours Room Temperature |
| 0.05% Tween ® 80 | 176 | 239 |

TABLE 5-continued

| Light Scattering Turbidity Assay | | |
|---|---|---|
| Formulation | Initial Scattering | Scatter After 4 Hours Room Temperature |
| 2% sucrose pH 6.5 | | |
| 0.2% Tween ® 80<br>1% sucrose pH 6.5 | 23 | 30 |
| 0.1% MaPEG<br>1% sucrose pH 6.5 | 56 | 61 |
| 0.02% Tween ® 80<br>1% sucrose pH 3.5 | 20 | 8 |
| 0.1% Tween ® 80<br>1% sucrose pH 3.5 | 29 | 0 |

Example 12

Representative formulations of this invention (1 mg/ml of IL-2) prepared essentially as described in Example 9 are listed in Table 6 with bioactivity results according to the HT-2 cell proliferation assay as described in Gillis et al., supra. The results are an average of three samples of each representative formulation. Bioactivity data were collected at the start of the stability data and at 5 weeks; the samples were maintained respectively at 4° C., 25° C. and 37° C. As the results in Table 6 indicate, the bioactivity of the formulations remained essentially constant over time and with increased storage temperature. The reconstituted sample formulations had the same bioactivity as preformulated IL-2 extracted and purified according to Example 9.

TABLE 6

| Bioactivity Data in U/mg | | | | |
|---|---|---|---|---|
| | | Five Weeks | | |
| Formulation | Initial | 4° C. | 25° C. | 37° C. |
| 0.05% Tween ® 80<br>2% sucrose | $1.3 \times 10^7$ | $1.3 \times 10^7$ | $1.3 \times 10^7$ | $1.3 \times 10^7$ |
| 0.1% MaPEG<br>1% sucrose | $1.6 \times 10^7$ | $1.4 \times 10^7$ | $1.2 \times 10^7$ | $1.4 \times 10^7$ |

Conclusion

In summary, it can be seen that the IL-2 formulations of the present invention containing, as stabilizing agents, biocompatible non-ionic polymeric detergents, screened according to the processes of the instant invention, are desirable, stable pharmaceutical compositions. Such compositions further can comprise a polyol as a bulking agent and be lyophilized. Formulation processes are also described herein which result in formulations having very low level of aggregates and minimal or no amounts of strong detergent solubilizing agents such as SDS. The formulations of this invention are further non-toxic and have good shelf life.

Deposits

As mentioned above, a culture of E. coli K12/MM294-1 carrying plasmid pLW45 was deposited at the American Type Culture Collection 12301 Parklawn Drive, Rockville, MD 20852, US, on Mar. 4, 1984 under ATCC. No. 39,626.

Said deposit was made pursuant to a contract between the ATCC and the assignee of this patent application, Cetus Corporation. The contract with the ATCC provides for permanent availability of said strain and progeny thereof to the public upon issuance of a U.S. Pat. related to this application describing and identifying the deposit or upon the publication or laying open to the public of any U.S. or foreign patent application, whichever comes first, and for the availability of the strain and the progeny thereof to one determined by the U.S. Commissioner of Patents and Trademarks to be entitled thereto according to 35 USC §122 and the Commissioner's rules pursuant thereto (including 37 CFR §1.14 with particular reference to 886 OG 638). The assignee of the present application has agreed that if the strain on deposit should die or be lost or destroyed when cultivated under suitable conditions, it will be promptly replaced upon notification with a viable culture of the same strain.

The deposit agreement under the terms of the Budapest Treaty assures that said culture deposited will be maintained in a viable and uncontaminated condition for a period of at least five years after the most recent request for the furnishing of a sample of the deposited microorganism was received by the ATCC and, in any case, for a period of at least 30 years after the date of the deposit.

The strain has been made available since May 21, 1985. Availability of the deposited strain is not to be construed as a license to practice the invention in contravention of the rights granted under the authority of any government in accordance with its patent laws.

Also, the present invention is not to be considered limited in scope by the strain deposited, since the deposited embodiment is intended only to be illustrative of particular aspects of the invention. Any microorganism strain which is functionally equivalent to that deposited is considered to be within the scope of this invention. Further, various modifications of the invention in addition to those shown and described herein apparent to those skilled in the art from the preceding description are considered to fall within the scope of the appended claims.

What is claimed is:

1. An aqueous, stable pharmaceutical composition of matter suitable for parenteral administration to animals or humans comprising a therapeutically effective amount of recombinant interleukin-2 (IL-2) protein dissolved in solution having an inert carrier medium comprising as a stabilizer, an effective amount of one or more biocompatible non-ionic polymeric detergents selected from the group consisting essentially of: octylphenoxy polyethoxy ethanol compounds; polyethylene glycol monostearate compounds: and polyoxyethylene sorbitan fatty acid esters.

2. A composition according to claim 1 which is either in liquid form or lyophilized.

3. A composition according to claim 2 which is lyophilized in a crystalline environment.

4. A composition according to claim 2 which is lyophilized in an amorphous environment.

5. A composition according to claim 1 wherein said octylphenoxy polyethoxy ethanol compounds have the formula

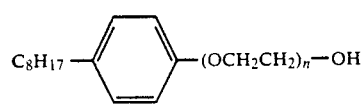

wherein n is an integer from about 15 to about 50; said polyethylene glycol monostearate compounds have the formula

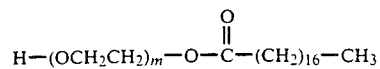

wherein m is an integer from about 10 to about 200; and said polyoxyethylene sorbitan fatty acid esters have the formula

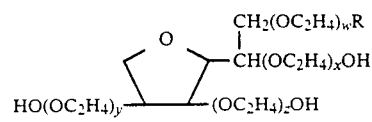

wherein the sum of the integers w, x, y and z equals 20 and R is an alkyl group having from about 10 to about 20 carbon atoms.

6. A composition according to claim 5 wherein n is an integer from about 25 to about 45; m is an integer from about 50 to about 150; and R is a fatty acid having from about 12 to about 18 carbons.

7. A composition according to claim 6 wherein n is an integer from about 30 to about 40; m is an integer from about 75 to about 125; and R is a fatty acid selected from the group consisting of lauric acid and oleic acid.

8. A composition according to claim 7 wherein the non-ionic detergents are selected from the group consisting of Triton ® X405, Triton ® X305, PEG (4000) monostearate, Tween ® 80 and Tween ® 20.

9. A composition according to claim 1 wherein the concentration (v/v or wt/v) range of said biocompatible non-ionic polymeric detergents is from about 0.001% to about 5%.

10. A composition according to claim 2 which is lyophilized and wherein said carrier medium further comprises a bulking agent.

11. A composition according to claim 10 wherein said bulking/stabilizing agent is selected from the group consisting of: sucrose, fructose, dextrose, maltose, glucose, dextran, mannitol, sorbitol, inositol, galactitol, xylitol, lactose, trehalose, human serum albumin and bovine serum albumin.

12. A composition according to claim 10 wherein said carrier medium further comprises a buffer which maintains the composition in a physiologically acceptable pH range.

13. A composition according to claim 12 wherein the bulking agent is mannitol in a concentration (wt/vol) range of from about 0.025% to about 10%, the buffer is glycine or phosphate in a concentration range of from about 10 mM to about 50 mM, and the lyophilization is in a crystalline environment.

14. A composition according to claim 12 wherein the bulking agent is a polyol sugar in a concentration (wt/vol) range of from about 0.025% to about 10%; said buffer is citrate in a concentration range of from about 10 mM to about 50 mM; the lyophilization is in an amorphous environment; and the pH range of the formulation is from about 3 to about 7.

15. A composition according to claim 14 wherein the polyol sugar is in a concentration range of from about 0.05% to about 7% and is selected from the group consisting of sucrose, dextrose, lactose, maltose, glucose, trehalose and fructose; wherein the citrate buffer is in a concentration range of from about 10 mM to about 20 mM; and wherein the pH range is from about 3.5 to about 6.5.

16. A composition according to claim 14 wherein the recombinant IL-2 (IL-2) is in a concentration range of from about 0.1 mg/ml to about 2 mg/ml of the carrier medium; the non-ionic detergent is in a concentration (v/v or wt/v) range of from about 0.005% to about 3% and is selected from the group consisting of Tween® 20, Tween® 80 and MaPEG; the bulking agent is sucrose in a concentration (wt/vol) range of from about 0.05% to about 7%; and the citrate buffer is in a concentration of about 10 mM; and wherein the pH range is from about 3 to about 4, or from about 6 to about 6.5.

17. A composition according to claim 16 wherein the IL-2 is des-ala$_1$-IL-2$_{ser125}$ in a concentration range of from about 0.125 mg/ml to about 1 mg/ml of the carrier medium.

18. A composition according to claim 12 wherein the bulking agent is a combination of mannitol and sucrose in a volume ratio of from about 20/1 to about 1/1, and the lyophilization is in an amorphous environment.

19. A composition according to claim 12 wherein the buffer is citrate in a concentration range from about 10 mM to about 50 mM and the pH is from about 3.5 to about 6.5, and the lyophilization is in an amorphous environment.

20. A composition according to claim 1 wherein the recombinant IL-2 is des-ala$_1$-IL-2$_{ser125}$ in a concentration range of from about 0.05 mg/ml to about 10 mg/ml of the carrier medium.

21. A composition according to claim 1 wherein the formulation is suitable for intravenous administration.

22. A composition according to claim 8 wherein the formulation is suitable for intravenous administration.

23. A composition according to claim 16 wherein the formulation is suitable for intravenous administration.

* * * * *